United States Patent
Glick et al.

(10) Patent No.: US 8,993,559 B2
(45) Date of Patent: Mar. 31, 2015

(54) USE OF IBOGAMINE CONGENERS FOR TREATING OBESITY

(75) Inventors: Stanley D. Glick, Delmar, NY (US); Isabelle M. Maisonneuve, Delmar, NY (US); Olga D. Taraschenko, Albany, NY (US)

(73) Assignee: Albany Medical College, Albany, NY (US)

( * ) Notice: Subject to any disclaimer, the term of this patent is extended or adjusted under 35 U.S.C. 154(b) by 846 days.

(21) Appl. No.: 12/360,434

(22) Filed: Jan. 27, 2009

(65) Prior Publication Data

US 2009/0281134 A1 Nov. 12, 2009

Related U.S. Application Data

(60) Provisional application No. 61/023,977, filed on Jan. 28, 2008.

(51) Int. Cl.
*A61K 31/44* (2006.01)
*A61K 31/55* (2006.01)

(52) U.S. Cl.
CPC ..................... *A61K 31/55* (2013.01)
USPC .................. 514/214.03; 514/214.02; 514/281

(58) Field of Classification Search
CPC ........................... A61K 31/55; A61K 31/4748
USPC .................. 514/281, 214.02, 214.03
See application file for complete search history.

(56) References Cited

U.S. PATENT DOCUMENTS

| 6,211,360 B1 | 4/2001 | Glick et al. |
| 2003/0199496 A1 | 10/2003 | Simon |

OTHER PUBLICATIONS

International Search Report for International Patent Application No. PCT/US09/32093 (Apr. 28, 2009).

(Continued)

*Primary Examiner* — Shengjun Wang
(74) *Attorney, Agent, or Firm* — LeClairRyan, a Professional Corporation

(57) ABSTRACT

The present invention relates to a method of treating obesity in a subject by administering to the subject a compound having the formula:

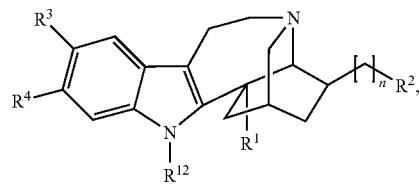

wherein n is from 0 to 8; $R^1$ is $CH_2OH$, $CH(OH)R^5$, $CH_2OR^5$, $CO_2R^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$; $R^2$ is H, unsubstituted or substituted alkyl, YH, $YR^8$, $YR^8R^9$, $YR^8YR^9YR^{10}$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, or $NR^8C(O)R^9$; $R^3$ and $R^4$ are the same or different and are selected from the group consisting of H, halogens, unsubstituted or substituted alkyl, OH, $OR^{10}$, $NH_2$, $NHR^{10}$, $NR^{10}R^{11}$, $NHC(O)R^{10}$, or $NR^{10}C(O)R^{11}$; $R^5$, $R^6$, $R^7$, $R^8$, $R^9$, $R^{10}$, and $R^{11}$ are the same or different and are selected from the group consisting of H, unsubstituted alkyl, substituted alkyl, unsubstituted aryl and substituted aryl; $R^{12}$ is selected from the group consisting of H, unsubstituted alkyl, and substituted alkyl; and Y is O or S; and pharmaceutically acceptable salts thereof.

33 Claims, 14 Drawing Sheets

(56) References Cited

OTHER PUBLICATIONS

Written Opinion of the International Searching Authority for International Patent Application No. PCT/US09/32093 (Mar. 17, 2009).
Rezvani et al., "Plant Derivatives in the Treatment of Alcohol Dependency," Pharmacology Biochemistry and Behavior 75:593-606 (2003).
European Search Report for European Patent Application No. 09706516.3 (Jul. 27, 2011).
Davis et al., "Sensitivity to Reward: Implications for Overeating and Overweight," Appetite 42:131-138 (2004).
Thomsen et al., "Lorcaserin, a Novel Selective Human 5-Hydroxytryptamine2C Agonist: in Vitro and in Vivo Pharmacological Characterization," The Journal of Pharmacology and Experimental Therapeutics, 325(2):577-587 (2008).

USE OF IBOGAMINE CONGENERS FOR TREATING OBESITY

This application claims benefit of U.S. Provisional Patent Application Ser. No. 61/023,977, filed Jan. 28, 2008, which is hereby incorporated by reference in its entirety.

GOVERNMENT SUPPORT

This invention was made with the support of the National Institute on Drug Abuse grant DA 016283. The Federal Government has certain rights in the invention.

FIELD OF THE INVENTION

The present invention relates to the use of ibogamine congeners for treating obesity.

BACKGROUND OF THE INVENTION

Obesity, a source of significant morbidity and increased mortality of the U.S. population, is among major public health problems in the country. Today's epidemic of obesity and associated disorders shows no signs of slowing down and threatens to undo the improvements in American health statistics achieved by reductions in cardiovascular morbidity. See Yach, D., et al., *Nat. Med.*, 12: 62-66 (2006). Needless to say, the benefits from losing weight are both medical and cosmetic, and since the majority of obese patients are excellent candidates for pharmacological treatments, the "race is on for the pill to control obesity". See Yach, D., et al., *Nat. Med.*, 12: 62-66 (2006). Despite these many efforts and a critical demand for safe and effective agents, there are only few agents currently approved by the FDA and available for clinical use in obese patients. See Bray, G. A., et al., *Pharmacol. Rev.*, 59: 151-184 (2007).

Considerable evidence exists that an increase in sugar consumption and drinking of sweetened substances can lead to obesity in humans. See Bray, G. A., et al., *Am. J. Clin. Nutr.*, 79: 537-543 (2004) and Bray, G. A., et al., *Am. J. Clin. Nutr.*, 55: 151 S-154S (1992). Thus, several animals models based on consumption of palatable fluids were developed to assess different aspects of excessive eating behavior and obesity. See Speakman, J., et al., *Obes. Rev.*, 8 Suppl 1: 55-61 (2007). For example, intermittent sugar intake models have been applied to study compulsive bingeing behavior (see Avena, N. M., et al., *Neurosci. Biobehav. Rev.*, (2007)), while continuous sugar intake models have been used to assess body weight dynamics and its hormonal regulation (see Bock, B. C., et al., *Physiol Behav.*, 57: 659-668 (1995)). Furthermore, operant administration of sucrose and other sweet solutions has been previously utilized to assess appetitive and motivational aspects of aberrant eating behavior. See Sclafani, A., *Physiol Behav.*, 87: 734-744 (2006) and Sclafani, A., et al., *Physiol Behav.*, 79: 663-670 (2003).

Mesolimbic dopamine is critically involved in mediation of food reward (see Berridge, K. C., *Neurosci. Biobehav. Rev.*, 20:1-25 (1996)), satiety and expression of ingestive motor behavior. See Berthoud, H. R., *Neurosci. Biobehav. Rev.*, 26: 393-428 (2002). Ingestion of sucrose or saccharine were shown to increases dopamine release in the nucleus accumbens (see Glick, S. D., et al., *Eur. J. Pharmacol.*, 537: 94-98 (2006); Mark, G. P., et al., *Brain Res.*, 551: 308-310 (1991); and Rada, P., et al., *Neuroscience*, 134: 737-744 (2005)), while cessation of chronic intake of glucose precipitated a withdrawal-like decrease of dopamine release similar to that observed in morphine-dependent rats. See Colantuoni, C., et al., *Obes. Res.*, 10: 478-488 (2002). Similarities between the neurochemical and behavioral consequences of excessive sugar consumption and addictive drugs lead to the concept of "sugar addiction". See Avena, N. M., et al., *Neurosci. Biobehav. Rev.*, (2007).

18-Methoxycoronaridine (18-MC), a potential anti-addictive agent and a selective antagonist of α3β4 nicotinic receptors, has been previously shown to attenuate sensitized morphine-induced dopamine release in the nucleus accumbens of morphine-experienced rats. Furthermore, systemic pretreatment with 18-MC has been shown to reduce the intravenous self-administration of morphine and other drugs (see Glick, S. D., et al., *Brain Res.*, 719: 29-35 (1996) and Glick, S. D., et al., *Neuroreport*, 11: 2013-2015 (2000)) and alleviate several signs of acute opioid withdrawal in rats. See Rho, B., et al., *Neuroreport*, 9: 1283-1285 (1998). Given the significant role of dopamine in compulsive eating behavior and development of obesity, the current studies were undertaken to assess the effects of 18-MC on operant self-administration of sucrose, consumption of palatable fluids as well as weight gain of rats.

The present invention is directed to overcoming the deficiencies in the art.

SUMMARY OF THE INVENTION

The present invention relates to a method of treating obesity in a subject by administering to the subject a compound having the formula:

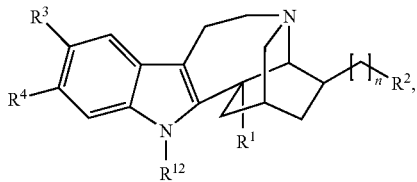

wherein n is from 0 to 8; $R^1$ is $CH_2OH$, $CH(OH)R^5$, $CH_2OR^5$, $CO_2R^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$; $R^2$ is H, unsubstituted or substituted alkyl, YH, $YR^8$, $YR^8R^9$, $YR^8YR^9YR^{10}$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, or $NR^8C(O)R^9$; $R^3$ and $R^4$ are the same or different and are selected from the group consisting of H, halogens, unsubstituted or substituted alkyl, OH, $OR^{10}$, $NH_2$, $NHR^{10}$, $NR^{10}R^{11}$, $NHC(O)R^{10}$ or $NR^{10}C(O)R^{11}$; $R^5$, $R^6R^7$, $R^8$, $R^9$, $R^{10}$, and $R^{11}$ are the same or different and are selected from the group consisting of unsubstituted alkyl, substituted alkyl, unsubstituted aryl and substituted aryl; $R^{12}$ is selected from the group consisting of H, unsubstituted alkyl, and substituted alkyl; and Y is O or S; and pharmaceutically acceptable salts thereof.

There are only a few available pharmacological treatments for obesity, and all have limited efficacy. Although amphetamine-like stimulants (e.g., methamphetamine, phentermine, diethylpropion), all releasing catecholamines, are effective appetite-suppressants, side effects (including addiction) are numerous, and tolerance to the anorexia occurs within several weeks; moreover, maximal weight loss is modest (10-15 lbs) and is usually negated soon after the drug is discontinued. Phenylpropanolamine, the one member of this group that was long available over-the-counter (approved by the FDA in 1939), has lower stimulant potency but was taken off the market in 2000 owing to cardiovascular toxicity in women. While structurally related to amphetamine, fenfluramine and its active enantiomer dexfenfluramine are nonstimulants and release serotonin; although fenfluramine was available for nearly 25 years, both drugs were taken off the market in 1997 due to cardiac and pulmonary toxicity. Sibutramine, introduced in 1997, inhibits reuptake of norepinephrine, serotonin, and, to a lesser extent, dopamine. Its efficacy is no better than the older agents and its use is limited because of its tendency to induce or exacerbate hypertension. Most recently, rimonabant, an agent that blocks cannabinoid CB1 receptors, has been used as an appetite suppressant in several European countries; however, because severe depression is a fairly common side effect, the FDA has indicated that rimonabant will not likely be approved in this country. Orlistat, the only other agent now available for obesity treatment, blocks gastrointestinal lipases and thereby reduces absorption of fatty acids; however, its long-term efficacy is limited, being similar to that of the appetite suppressants. Clearly, new and better anti-obesity agents are needed, and 18-MC may be the first of a new generation of such agents.

DETAILED DESCRIPTION

Figure 1:
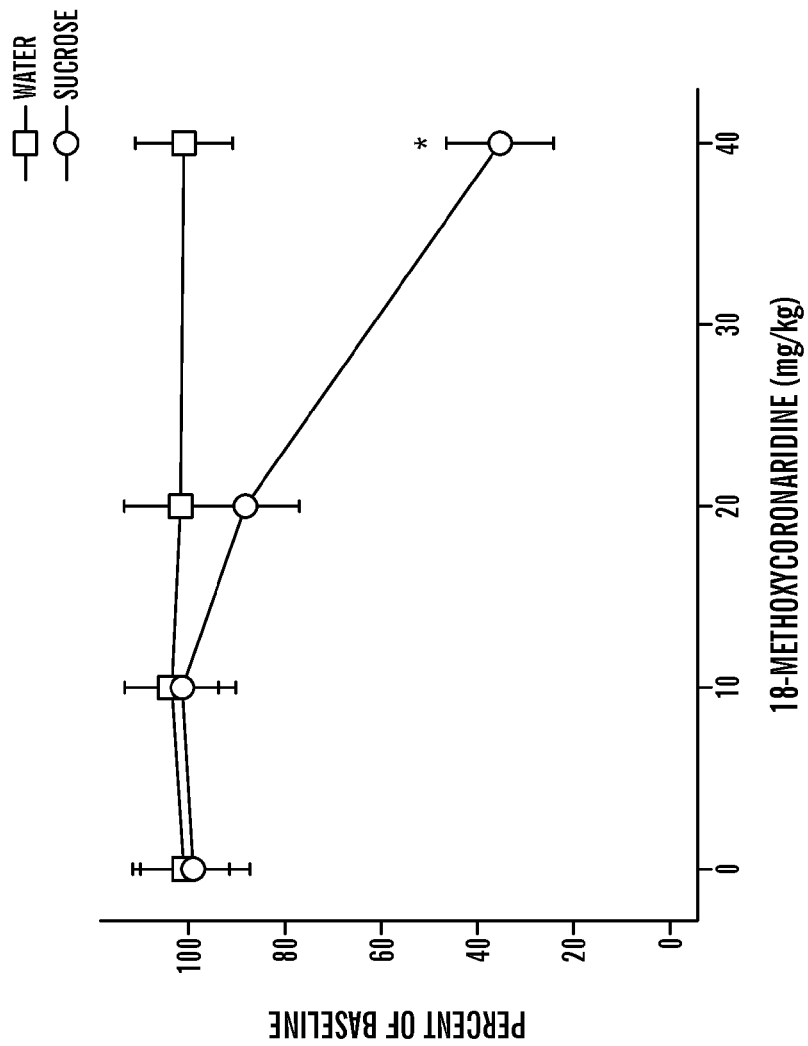
FIG. 1 is a graph showing the effect of 18-methoxycoronaridine (18-MC) on operant self-administration of sucrose and water as a percent of baseline. n=6/group. *, p<0.005 vs saline, Newman-Keuls test.

The present invention relates to a method of treating obesity in a subject by administering to the subject a compound having the formula:

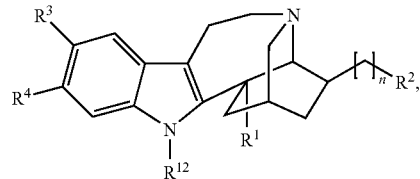

wherein n is from 0 to 8; $R^1$ is $CH_2OH$, $CH(OH)R^5$, $CH_2OR^5$, $CO_2R^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$; $R^2$ is H, unsubstituted or substituted alkyl, YH, $YR^8$, $YR^8R^9$, $YR^8YR^9YR^{10}$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, or $NR^8C(O)R^9$; $R^3$ and $R^4$ are the same or different and are selected from the group consisting of H, halogens, unsubstituted or substituted alkyl, OH, $OR^{10}$, $NH_2$, $NHR^{10}$, $NR^{10}R^{11}$, $NHC(O)R^{10}$, or $NR^{10}C(O)R^{11}$; $R^5$, $R^6$, $R^7$, $R^8$, $R^9$, $R^{10}$, and $R^{11}$ are the same or different and are selected from the group consisting of H, unsubstituted alkyl, substituted alkyl, unsubstituted aryl and substituted aryl; $R^{12}$ is selected from the group consisting of H, unsubstituted alkyl, and substituted alkyl; and Y is O or S; and pharmaceutically acceptable salts thereof.

The term obesity implies an excess of adipose tissue. In this context, obesity is best viewed as any degree of excess adiposity that imparts a health risk. The distinction between normal and obese individuals can only be approximated, but the health risk imparted by obesity is probably a continuum with increasing adiposity. However, in the context of the present invention, individuals with a body mass index (BMI=body weight in kilograms divided by the square of the height in meters) above 25 are to be regarded as obese. When energy intake exceeds energy expenditure, the excess calories are stored in adipose tissue, and if this net positive balance is prolonged, obesity results, i.e. there are two components to weight balance, and an abnormality on either side (intake or expenditure) can lead to obesity.

Certain embodiments of the present invention relate to compounds having the formula:

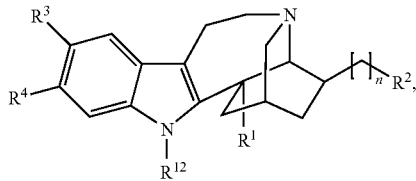

In certain embodiments, $R^1$ is selected from the group consisting of an alcohol, an ether, an ester, an amide, a hydrazide, a cyanide, or a ketone. Suitable alcohols include $CH_2OH$ $CH(OH)R^5$, suitable ethers include those having the formulae $CH_2OR^5$, and suitable esters include those having the formulae $CO_2R^5$. Amides can be unsubstituted, such as $C(O)NH_2$, monosubstituted, such as, $C(O)NHR^5$, or disubstituted, such as $C(O)NR^5R^6$. Suitable hydrazides include unsubstituted hydrazides, having the formula $C(O)NHNH_2$, monosubstituted hydrazides, having the formulae $C(O)NHNHR^5$ or $C(O)NR^5NH_2$, disubstituted hydrazides, having the formulae $C(O)NHNR^5R^6$ or $C(O)NR^5NHR^6$, or trisubstituted hydrazides, having the formulae $C(O)NR^5NR^6R^7$. The hydrazides can also contain an amide functionality at the terminal nitrogen, such as hydrazides having the formulae $C(O)NHNH(C(O)R^5)$, $C(O)NHNR^5(C(O)R^6)$, $C(O)NR^5NH(C(O)R^6)$, or $C(O)NR^5NR^6(C(O)R^7)$. Suitable ketones are those where $R^1$ is $C(O)R^5$.

$R^5$, $R^6$, and $R^7$ can be either H, unsubstituted alkyl, such as, methyl, ethyl, n-propyl, iso-propyl, n-butyl, sec-butyl, tert-butyl, n-pentyl, sec-pentyl, and neo-pentyl, hexyl, heptyl, octyl, nonyl, decyl, dodecyl, dodecyl, and the like, or substituted with any of a number of known substituents, such as sulfo, carboxy, cyano, halogen (e.g., fluoro, chloro), hydroxy, alkenyl (e.g. allyl, 2-carboxy-allyl), alkoxy (e.g., methoxy, ethoxy), aryl (e.g., phenyl, p-sulfophenyl), aryloxy (e.g., phenyloxy), carboxylate (e.g., methoxycarbonyl, ethoxycarbonyl), acyloxy (e.g. acetyloxy), acyl (e.g. acetyl, propionyl), and others known to those skilled in the art. In addition, substituted alkyls include arylalkyls, such as 2-phenyleth-1-yl, 2-phenylprop-1-yl, benzyl, and arylalkyls bearing substitutents on the aromatic ring, such as 2-(5-chlorophenyl)prop-1-yl, N-piperidino, N-pyrrolidino, and N-morpholino. Each of $R^5$, $R^6$, and $R^7$ can be the same or different and the combination is selected primarily with consideration given to the substitution's effect on water-solubility and biological compatibility, although other factors, such as availability of starting materials and synthetic ease may enter into the selection.

Suitable esters include ethyl ester, benzyl ester, dialkylaminoalkyl esters, and, preferably, methyl ester. Amides can be, for example, N-methylamide, N-ethylamide, N,N-dimethylamide, N,N-diethylamide, N-methyl-N-ethylamide, and peptides derived from amino acids and their esters or amides. $R^2$ can also be a hydrazide, such as $N^1,N^1$-dimethylhydrazide, $N^1,N^{11}$-dimethylhydrazide, or preferably, unsubstituted hydrazide.

The ibogamine skeleton can be unsubstituted at the C20 position (such as in the case of desethylcoronaridine), or it can be substituted at the C20 position with an alkyl or, preferably, a derivatized alkyl. The alkyl chain, represented in the above formula by $(CH_2)_n$, can have from zero to eight carbons, inclusive, such as methyl, ethyl, propyl, butyl, pentyl, hexyl, heptyl, and octyl, and is preferably ethyl. The alkyl chain is derivatized with $R^2$ at the terminal carbon of the alkyl chain (or, in the case where n is zero, at the C20 carbon). $R^2$ is selected from the group consisting of a hydrogen, a substituted or unsubstituted alkyl, a hydroxyl, an ether, a thiol, a thioether, an amine, or an acid or thioacid derivative. In cases where n is zero, $R^2$ is preferably H or substituted or unsubstituted alkyl. Illustrative examples of suitable substituted or unsubstituted alkyls include those given for $R^5$, $R^6$, and $R^7$, above. Suitable ethers and thioethers have the formulae $OR^8$ and $SR^8$, respectively. Suitable amines include unsubstituted amines ($NH_2$), monosubstituted amines ($NHR^8$), or disubstituted amines ($NR^8R^9$). Acid or thioacid derivatives can have the formulae $OC(O)R^8$, $SC(O)R^8$, $C(O)NH_2$, $C(O)SR^8$, $C(O)OR^8$, $C(O)NHR^8$, $C(O)NR^8R^9$, $NHC(O)R^8$, or $NR^8C(O)R^9$. In each of the above, $R^8$ and $R^9$ can be the same or different and are selected from the group consisting of substituted or unsubstituted alkyl, examples of which are the same as those given for $R^5$, $R^6$, and $R^7$, above. As an illustration, suitable ethers and thioethers include methoxy, ethoxy, propoxy, butoxy, pentoxy, methoxyethoxymethyl ether ($OCH_2OCH_2CH_2OCH_3$), methylthio, ethylthio, dimethylaminoalkoxy, and sugar acetals, such as a glucoside. Suitable amine derivatives include methylamino, ethylamino, propylamino, butylamino, pentylamino, dimethylamino, diethylamino, dipropylamino, dibutylamino, methylethylamino, methylpropylamino, methylbutylamino, ethylpropylamino, ethylbutylamino, propylbutylamino, pyrrolidino, piperidino, and morpholino. Acid or thioacid derivatives can be, for example, $OC(O)CH_3$, $OC(O)CH_2CH_3$, $OC(O)(CH_2)_2CH_3$, $OC(O)(CH_2)_3CH_3$, $OC(O)(CH_2)_4CH_3$, $OC(O)(CH_2)_5CH_3$, $OC(O)(CH_2)_6CH_3$, $OC(O)(CH_2)_{10}CH_3$, $OC(O)(CH_2)_{12}CH_3$, $SC(O)(CH_2)_{20}CH_3$, $SC(O)CH_3$, $SC(O)CH_2CH_3$, $SC(O)(CH_2)_2CH_3$, $SC(O)(CH_2)_3CH_3$, $SC(O)(CH_2)_4CH_3$, $SC(O)(CH_2)_5CH_3$, $SC(O)(CH_2)_6CH_3$, $SC(O)(CH_2)_{10}CH_3$, $SC(O)(CH_2)_{12}CH_3$, $SC(O)(CH_2)_{20}CH_3$, $NHC(O)CH_3$, $NHC(O)CH_2CH_3$, $NHC(O)(CH_2)_2CH_3$, $NHC(O)(CH_2)_3CH_3$, $NHC(O)(CH_2)_{10}CH_3$, $NHC(O)(CH_2)_{12}CH_3$, $NHC(O)(CH_2)_{20}CH_3$, $N(CH_3)C(O)CH_3$, $N(CH_3)C(O)CH_2CH_3$, $N(CH_3)C(O)(CH_2)_2CH_3$, $N(CH_3)C(O)(CH_2)_3CH_3$, $N(CH_3)C(O)(CH_2)_{10}CH_3$, $N(CH_3)C(0)(CH_2)_{12}CH_3$, $N(CH_3)C(O)(CH_2)_{20}CH_3$, and esters and amides derived from amino acids and amino acid amides.

$R^3$ and $R^4$ can be the same or they can be different. Each can be selected from hydrogen, halide (such as fluoride, chloride, bromide, and iodide), alkyl, hydroxy, ether, or amine. The alkyl can be substituted or unsubstituted and is exemplified by the substituted or unsubstituted alkyls used to illustrate $R^5$, $R^6$, and $R_7$. Suitable ethers have the formulae $OR^{10}$ and suitable amines include unsubstituted amines ($NH_2$), monosubstituted amines ($NHR^{10}$), or disubstituted amines ($NR^{10}R^{11}$). In each of the above, $R^{10}$ and $R^{11}$ can be the same or different and are selected from the group consisting of substituted or unsubstituted alkyl, examples of which are the same as those given for $R^5$, $R^6$, and $R^7$, above. As an illustration, $R^3$, $R^4$, or both $R^3$ and $R^4$ can be methoxy, ethoxy, propoxy, butoxy, pentoxy, methoxyethoxymethyl ether ($OCH_2OCH_2CH_2OCH_3$), methylamino, ethylamino, propylamino, butylamino, pentylamino, dimethylamino, diethylamino, dipropylamino, dibutylamino, methylethylamino, methylpropylamino, methylbutylamino, ethylpropylamino, ethylbutylamino, propylbutylamino, and arylalkyl, such as benzyl. In addition, the $R^3$ and $R^4$ substituents can be linked via an alkylene, such as methylene or ethylene, to form a five- or six-membered ring, such as where $R^3$ and $R^4$, together, are —OCH$_2$O—, —OCH$_2$CH$_2$O—, —NHCH$_2$O—, —NHCH$_2$CH$_2$O—, —NHCH$_2$NH—, and —NHCH$_2$CH$_2$NH—.

R$^{12}$ can be a hydrogen, a substituted alkyl, such as an arylalkyl, or an unsubstituted alkyl. Suitable unsubstituted and substituted alkyls include those used to exemplify R$^5$, R$^6$, and R$^7$, above.

Illustrative examples of compounds of the present invention are as follows:
18-hydroxycoronaridine;
18-hydroxyvoacangine;
18-hydroxyconopharyngine;
16-ethoxycarbonyl-18-hydroxyibogamine;
16-ethoxycarbonyl-18-hydroxyibogaine;
16-ethoxycarbonyl-18-hydroxyibogaline;
16-hydroxymethyl-18-hydroxyibogamine;
16-hydroxymethyl-18-hydroxyibogaine;
16-hydroxymethyl-18-hydroxyibogaline;
18-methoxycoronaridine;
18-methoxyvoacangine;
18-methoxyconopharyngine;
16-ethoxycarbonyl-18-methoxyibogamine;
16-ethoxycarbonyl-18-methoxyibogaine;
16-ethoxycarbonyl-18-methoxyibogaline;
16-hydroxymethyl-18-methoxyibogamine;
16-hydroxymethyl-18-methoxyibogaine;
16-hydroxymethyl-18-methoxyibogaline;
18-benzyloxycoronaridine;
18-benzyloxyvoacangine;
18-benzyloxyconopharyngine;
16-ethoxycarbonyl-18-benzyloxyibogamine;
16-ethoxycarbonyl-18-benzyloxyibogaine;
16-ethoxycarbonyl-18-benzyloxyibogaline;
18-hydroxycoronaridine laurate;
18-hydroxyvoacangine laurate;
18-hydroxyconopharyngine laurate;
16-ethoxycarbonyl-18-hydroxyibogamine laurate;
16-ethoxycarbonyl-18-hydroxyibogaine laurate;
16-ethoxycarbonyl-18-hydroxyibogaline laurate;
18-hydroxycoronaridine acetate;
18-hydroxyvoacangine acetate;
18-hydroxyconopharyngine acetate;
16-ethoxycarbonyl-18-hydroxyibogamine acetate;
16-ethoxycarbonyl-18-hydroxyibogaine acetate;
16-ethoxycarbonyl-18-hydroxyibogaline acetate;
18-hydroxycoronaridine methoxyethoxymethyl ether;
18-hydroxyvoacangine methoxyethoxymethyl ether;
18-hydroxyconopharyngine methoxyethoxymethyl ether;
16-ethoxycarbonyl-18-hydroxyibogamine methoxyethoxymethyl ether;
16-ethoxycarbonyl-18-hydroxyibogaine methoxyethoxymethyl ether;
16-ethoxycarbonyl-18-hydroxyibogaline methoxyethoxymethyl ether;
and pharmaceutically acceptable salts thereof.

Particularly preferred are compounds having the formulae:

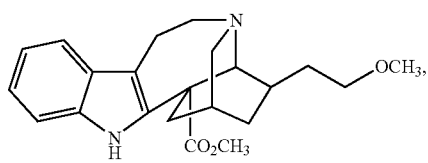

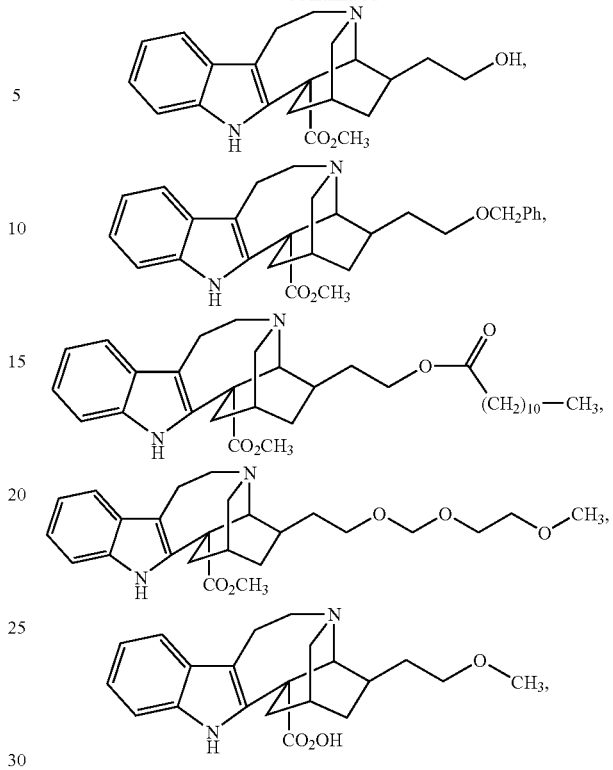

and pharmaceutically acceptable salts thereof.

As used herein, pharmaceutically acceptable salts are non-toxic salts which can be employed by those skilled in the art for in vivo use. Suitable pharmaceutically acceptable salts are the salts formed with inorganic acids, such as hydrochloric acid, sulfuric acid, nitric acid, and phosphoric acid, metal bicarbonates, such as sodium bicarbonate, monometal phosphates, such as monosodium phosphate, and dimetal phosphates, such as disodium phosphate. The salts can also be formed by reaction with organic acids, such as carboxylic acids or sulfonic acids. Suitable carboxylic acids include acetic, propionic, glycolic lactic, pyruvic, malonic, succinic, fumaric, malic, tartaric citric, cyclamic, ascorbic, maleic, hydroxymaleic, dihydroxymaleic, benzoic, phenylacetic, 4-aminobenzoic, anthranillic, cinnamic, salicyclic, 4-aminosalicylic, 2-phenoxybenzoic, 2-acetoxybenzoic, and mandelic acid. Suitable sulfonic acids are, for example, methanesulfonic, ethanesulfonic, and β-hydroxyethane-sulfonic acid.

As will be recognized by those skilled in the art, the compounds of the present invention have four chiral carbon centers in the ibogamine skeleton. As used herein, a "compound" of the present invention includes compounds having the aforementioned formulae without regard to the stereochemistry at these chiral centers. Accordingly, "compound" includes compounds which are racemic as well as to those which are optically pure with respect to the C20. In addition, the "compounds" of the present invention include those which are racemic and those which are optically pure with respect to the three bridgehead chiral carbons.

The compounds of the present invention can be synthesized using the methodology in U.S. Pat. No. 6,211,360 to Glick et al., which is hereby incorporated by reference in its entirety. As described in Bornmann (see Bornmann, et al., J. Org. Chem., 57:1752 (1992), which is hereby incorporated by reference in its entirety) by reacting an appropriate 3-substituted-3-(1,3-dioxolan-2-yl) butanal having the formula:

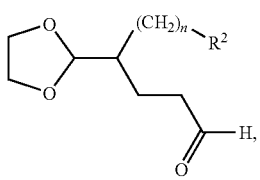

wherein n is from 0 to 8; $R^2$ is H, unsubstituted or substituted alkyl, YH, $YR^8$, $YR^8R^9$, $YR^8YR^9YR^{10}$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, or $NR^8C(O)R^9$; $R^8$ and $R^9$ are the same or different and are selected from the group consisting of unsubstituted or substituted alkyl; and Y is O or S with an indoloazepine having the formula:

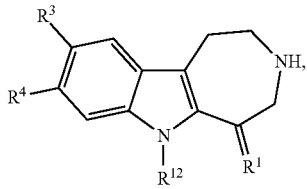

wherein $R^1$ is $CO^2R^5$, $C(O)NH_2$, $C(O)NHR^5$, $C(O)NR^5R^6$, $C(O)NHNH(C(O)R^5)$, $C(O)NHN(C(O)R^5)R^6$, $C(O)NHNR^5R^6$, $C(O)NR^5NH(C(O)R^6)$, $C(O)NR^5NR^6(C(O)R^7)$ or $C(O)NR^5NR^6R^7$; $R^3$ and $R^4$ are the same or different and are selected from the group consisting of H, halogens, unsubstituted or substituted alkyl, OH, $OR^{10}$, $NH(C(O)R^{10})$, $NR^{10}(C(O)R^{11})$ or $NR^{10}R^{11}$; $R^5$, $R^6$, $R^7$, $R^{10}$, and $R^{11}$ are the same or different and are selected from the group consisting of H, unsubstituted or substituted alkyl; and $R^{12}$ is selected from the group consisting of H unsubstituted alkyl, and substituted alkyl, under conditions effective to form a condensation product having the formula:

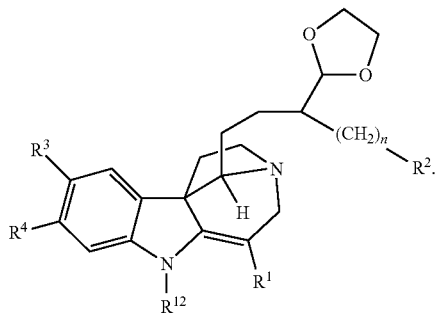

Typically, equimolar amounts of the two reactants are dissolved in an organic solvent and maintained at room temperature for 0.5 to 72 hours, preferably for 16 hours. Suitable solvents include alcohol solvents, such as methanol, ethanol, isopropanol, and n-butanol; ester-containing solvents, such as ethyl acetate and isopropyl acetate; ether solvents such as tetrahydrofuran, diglyme, and dioxane; chlorinated hydrocarbons, such as methylene chloride, chloroform, and carbon tetrachloride; aromatic hydrocarbons, such as benzene, toluene, and xylene; acetonitrile; pyridine; and dimethylformamide. Preferably, a solvent is chosen in which both reactants are substantially soluble. Methanol is particularly preferred.

After reaction is complete, the condensation product is treated in a suitable solvent with an equivalent amount of an appropriate arylalkyl containing a good leaving group, such as an arylalkyl tosylate, an arylalkyl mesylate, or an arylalkyl halide, preferably benzyl bromide, for 0.5 to 72 hours, preferably 16 hours, at 50° C. to 120° C., preferably at the reflux temperature of the solvent. Suitable solvents include lower alkanes, such as pentane, hexane, or petroleum ether; aromatic hydrocarbon solvents, such as benzene, toluene, and xylene; alcohols, such as methanol, ethanol, isopropanol, and n-butanol; and ether solvents, such as diethyl ether, diglyme, or tetrahydrofuran.

Treatment of the product, with an organic-soluble Lewis base, preferably triethylamine, produces a transient enamine acrylate having the formula:

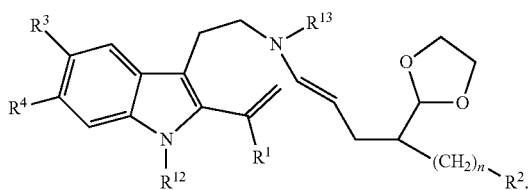

Typical solvents for the base treatment include alcohol solvents, such as methanol, ethanol, isopropanol, and n-butanol; ketone solvents, such as acetone, methyl ethyl ketone, and cyclopentanone; ester-containing solvents, such as ethyl acetate and isopropyl acetate; ether solvents, such as tetrahydrofuran, diglyme, and dioxane; chlorinated hydrocarbons, such as methylene chloride, chloroform, and carbon tetrachloride; acetonitrile; pyridine; and dimethylformamide. Preferably, a solvent is chosen in which both reactants are substantially soluble. Methanol is particularly preferred. Base treatment can be conducted at any temperature from room temperature to the boiling point of the solvent but is advantageously effected with slight heating preferably from 50° C. to 70° C. for from 1 to 10 hours.

The transient enamine acrylate spontaneously cyclizes to produce a versatiline derivative having the formula:

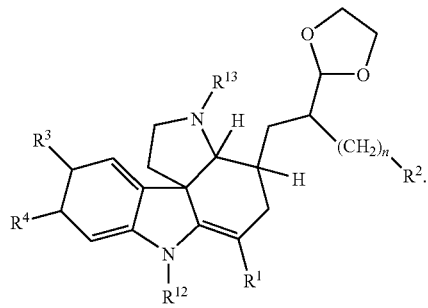

Alternatively, the versatiline derivative can be prepared in accordance with the method described by Kuehne. See Kuehne, et al., *J. Org. Chem.*, 58:4147 (1993), which is hereby incorporated by reference in its entirety. Briefly, the 3-substituted-3-(1,3-dioxolan-2-yl)butanal is treated with an N-arylalkyl derivative having the formula:

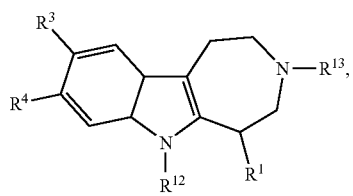

where $R^{13}$ is an arylalkyl, such as benzyl. Suitable solvents for the reaction include aromatic solvents, such as benzene, toluene, and xylene; ester-containing solvents, such as ethyl acetate and isopropyl acetate; ether solvents, such as tetrahydrofuran, diglyme, and dioxane; chlorinated hydrocarbons, such as methylene chloride, chloroform, and carbon tetrachloride; acetonitrile; pyridine; and dimethylformamide. Toluene is particularly preferred. The reaction is typically conducted at a temperature from 100° C. to 120° C. preferably at reflux.

Irrespective of the route used in its preparation, the versatiline derivative is then converted to a cleavamine having the formula:

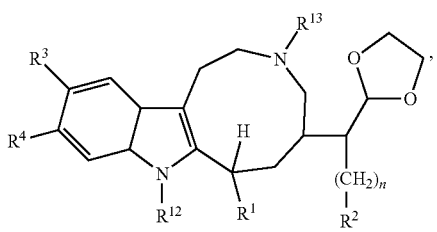

by reduction with, for example, sodium borohydride in an acidic solvent, preferably acetic acid. The reduction is effected by heating, preferably to a temperature between 80° C. and 110° C., more preferably between 85° C. and 95° C.

Reduction, preferably catalytic reduction using $H_2$ over palladium/carbon catalyst, followed by treatment with acidic alcohol, preferably with hydrochloric acid in methanol, followed by addition of a base, such as ammonium hydroxide, yields an enamine having the formula:

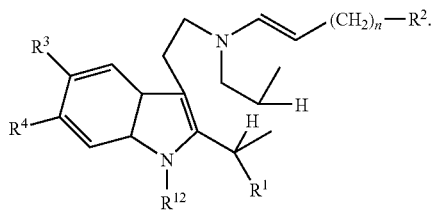

The enamine is then heated, preferably at between 80° C. and 120° C. for 4 to 12 hours in a suitable solvent, to produce a compound of the present invention having formula 1:

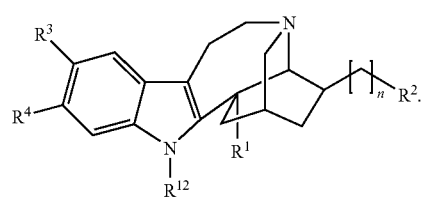

Suitable solvents include aromatic solvents, such as benzene, toluene, and xylene: ether solvents, such as tetrahydrofuran, diglyme, and dioxane; chlorinated hydrocarbons, such as methylene chloride, chloroform, and carbon tetrachloride; acetonitrile; pyridine; and dimethylformamide. Toluene is particularly preferred. Alternatively, the compound of the present invention can be prepared by storing the enamine under vacuum or in an inert atmosphere, such as under argon or nitrogen, for at least 12 hours, preferably 4 days to 6 days.

As an alternative to using a 3-substituted-(1,3-dioxolan)-2-yl)butanal, where $R^2$ is hydroxy, compounds of the present invention bearing a C18 hydroxyalkyl moiety (1 ($R^2$=OH)) can also be prepared by reduction of the corresponding C18 alkyl ester (such as, 1 ($R^2$=COOR$^5$)), for example, with a half-molar equivalent of lithium aluminum hydride or with diisobutylaluminum hydride. Compounds bearing the alkoxyalkyl moiety (1 ($R^2$=OR$^5$)) can likewise be prepared from the corresponding esters (1 ($R^2$=COOR$^5$)), such as by reduction with LiAlH$_4$/AlCl$_3$. In a similar manner, it can be advantageous to prepare compounds of the present invention having basic amines (such as 1 ($R^2$=NH$_2$ or $R^2$=NHR$^8$)) from the corresponding amides (such as 1 ($R^2$=NHC(O)R$^8$ or $R^2$=NR$^8$C(O)R$^9$)) by hydrolysis with aqueous acid rather that by starting with amine-containing 3-substituted-(1,3-dioxolan)-2-yl)butanal. The amide to amine conversion can also be effected by conventional procedures, such as with diisobutylaluminum hydride in an ether, preferably tetrahydrofuran ("THF") to give a substituted amine. Again, this alternative method is particularly advantageous when n is less than three.

Compounds having C16 hydroxy or alkoxymethyl substituents are prepared by reduction of the corresponding C16 ester, such as with LiAlH$_4$/THF to the C16 hydroxymethyl or with LiAlH$_4$/AlCl$_3$ to the C16 alkoxymethyl. Reduction of C16 amides with LiAlH$_4$ would provide C16 amines. C16 hydrazides containing basic nitrogens (such as 1 ($R^1$=C(O) NHNH$_2$, C(O)NHNR$^5$, C(O)NR$^5$NH$_2$, or C(O)NR$^5$NHR$^6$) can be prepared from the corresponding hydrazide carbamates, typically t-butyl carbamate, by hydrolysis with acids.

Subsequent to preparation, the compound of the present invention can optionally be purified by recrystallization, solvent extraction using, for example, a Soxhlet extraction apparatus, chromatography, such as HPLC or conventional column chromatography, or other conventional purification methods. In addition, prior to, subsequent to, or as an aid in isolation, the compounds of the present invention can be converted to the acid addition salt, such as by contacting a solution of the compound with an appropriate acid.

Preparation of the 3-substituted-(1,3-dioxolan-2-yl)butanal starting materials, is achieved by conventional methods. Typically these reactants are prepared by oxidation of a 2-substituted-4-hydroxybutyric ester. The latter can be obtained by alkylation of a allylmalonic ester with an alkyl halide and a base (e.g. sodium alkoxide) followed by decarboalkoxylation with LiCl, hydroboration with diborane or with borane dimethylsulfide complex, and oxidation with hydrogen peroxide and sodium hydroxide. Oxidation of the 4-hydroxy-2-substituted butanoic ester is achieved with dimethyl sulfoxide and oxalyl chloride. The resulting aldehyde is protected, preferably as its acetal with ethylene glycol. Reduction of the ester function, such as with LiAlH$_4$, is followed by oxidation of the resultant alcohol with dimethylsulfoxide and oxalyl chloride.

The indoloazepine starting material, with which the butanal is reacted, is typically prepared by methods which have been well-developed in the art. See Kuehne, et al., *J. Org. Chem.*, 43:3705 (1978); Kuehne, et al., *J. Org. Chem.*, 44:1063 (1979); Kuehne, et al., *J. Org. Chem.*, 45:3259 (1980); Kuehne, et al., *J. Org. Chem.*, 50:919 (1985); and Kuehne, et al., *J. Org. Chem.*, 56:513 (1991), which are hereby incorporated by reference in their entirety. Briefly, the indoloazepine starting material can be prepared by condensation of tryptamine with methyl 3-chloropyruvate. The resulting carboline is heated in pyridine to provide an unsaturated indoloazepine (vinylogous urethane). The latter is reduced with sodium cyanoborohydride.

When using the alternative route to the preparation of versatiline derivatives, the appropriately substituted $N_b$-benzylindoloazepine is prepared by alkylation of the above $N^b$—H indoloazepine with benzyl bromide and sodium carbonate. Alternatively, indoloazepines with substituents on the aromatic ring can be made by Fischer Indole synthesis from substituted phenylhydrazines and N-benzyl-4-piperidones, followed by reaction with t-butyl hypochlorite and thallium dimethyl malonate, and, then, with lithium chloride.

The compounds of the present invention are useful in treating subjects, such as mammals including humans, for obesity by administering the compounds to such subjects in an effective amount. The compounds of the present invention may be administered alone or in combination with suitable pharmaceutical carriers or diluents. The diluent or carrier ingredients should be selected so that they do not diminish the therapeutic effects of the compounds of the present invention.

The compounds of the present invention can be administered orally, topically, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions. Examples of parenteral administration are intraventricular, intracerebral, intramuscular, intravenous, intraperitoneal, rectal, and subcutaneous and subcutaneous administration.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

One aspect of the present invention is directed to therapeutically treating a subject suffering obesity.

It will be appreciated that the actual preferred amount of compound of the present invention used will vary according to the particular compound, the particular composition formulated, and the mode of application. Many factors that modify the action will be taken into account by those skilled in the art; e.g., body weight, sex, diet, time of administration, route of administration, rate of excretion, condition of the host, drug combinations, reaction sensitivities and severities and severity of disease. Administration can be carried out continuously or periodically within the maximum tolerated dose. Optimal application rates for a given set of conditions can be ascertained by those skilled in the art using conventional dosage administration tests in view of the above guidelines. Preferably the compound is administered in a dose from about 1.0 to about 80 mg/kg, preferably 10 to 40 mg/kg, of the subject's mass. Preferably, this dose of the compound is administered once daily.

The present invention is further illustrated by the following examples.

EXAMPLES

Example 1

Animals

Naïve female Sprague-Dawley rats (230-270 g; Taconic, Germantown, N.Y.) were housed individually and maintained on a normal 12 hr light cycle (light on/off at 7 a.m./7 p.m.) in the colony room. For all experiments, food (normal chow) and water were provided ad libitum. The experiments were conducted in accordance with the "Guide for the Care and Use of Laboratory Animals" (National Academy of Sciences, 1996).

Example 2

Drugs

18-MC (Albany Molecular Research, Albany, N.Y.) was dissolved in 0.01 M $NaH_2PO_4$ (vehicle). Sucrose (5%, 15% or 30%, wt/vol, MP Biomedicals, Inc., Solon, Ohio), saccharine sodium hydrate (0.1%, wt/vol, Sigma, St. Louis, Mo.), and sodium chloride (0.6%, wt/vol, Fisher Scientific, Fair Lawn, N.J.) were dissolved in water.

Example 3

Operant Sucrose Self-Administration Procedure

Rats were water deprived for 23 h so that shaping of the bar-press response could initially be accomplished by training rats to bar-press for water. Thereafter, in non-deprived rats, oral sucrose self-administration testing began with a 16-h nocturnal session followed by daily 1-h sessions, 5 days (Monday-Friday) a week. Rats were allowed access to two levers mounted 15 cm apart on the front wall of each operant test chamber (Coulbourn Instruments, Allentown, Pa.). A response on either of the two levers produced a sucrose reward (15% solution; 0.01 ml) on a FR1 TO 20 (fixed ratio 1 with a 20 sec time-out) schedule. After rates of sucrose self-administration stabilized (20% variation from one day to the next across 5 days), usually after 2 weeks of testing, 18-MC (10-40 mg/kg) or vehicle was administered i.p. 15 minutes before a test session. Each rat typically received two or three different treatments (in randomized order) spaced at least one week apart.

Example 4

Palatable Liquid Consumption

On the first day of the experiment, the regular cage tops were replaced with custom-made cage tops containing metal holders for two 100-ml graduated glass bottles (Lab Products Inc., Seaford, Del.); the bottles were placed approximately 2" apart. Different groups of rats were allowed 19-h (3.30 p.m.-10.30 a.m.) unlimited access to water and 5% sucrose, water and 0.1% saccharine, water and 0.6% saline, or water and water. The concentrations were chosen in accordance with previous reports using similar two-bottle drinking paradigms.

See Dess, N. K., *Physiol Behav.*, 69: 247-257 (2000) and Warwick, Z. S. et al., *Physiol Behav,* 60: 711-715 (1996), which are hereby incorporated by reference in their entirety. The animals were maintained on a normal chow during these sessions. The bottles with palatable fluids were removed at the end of the 19-h sessions, but water and chow remained always available. The consumption of palatable fluids and water during the sessions were recorded on a daily basis for four consecutive sessions: two initial baseline sessions, one treatment session and one port-treatment session. The baseline consumption levels of fluids were established during the initial two sessions; immediately before the third session, animals were injected with 18-MC (10, 20, or 40 mg/kg i.p.) or vehicle. To account for possible side preferences of rats, the bottle sides were switched daily; animals expressing strong side preferences during the baseline sessions were excluded from further analysis. Each animal was used for four weeks, receiving three different dosages of 18-MC and vehicle in random order.

Example 5

Weight Gain Paradigm: Sucrose-Drinking Animals

Animals were maintained on a regular chow and water for the duration of experiment (three weeks). On the first day of experiment, animals received additional bottle containing 30% sucrose solution which remained available for the following three weeks; the bottle sides were switched daily. The body weights of rats were recorded daily for the following two weeks immediately prior administration of 18-MC (20 mg/kg, i.p.) or vehicle. After the last 18-MC injection, the weights were monitored for the additional week.

Example 6

Weight Gain Paradigm: Water-Drinking Animals

Animals were allowed unlimited access to regular chow and water and were injected daily with 18-MC (20 mg/kg, i.p.) or vehicle for two weeks. Body weights were recorded immediately prior to injections and were also recorded for an additional week upon cessation of 18-MC treatment.

Example 7

Statistical Analysis

The operant self-administration data were analyzed by two-way ANOVA with reward (sucrose vs. water) and dose of 18-MC as the main factors. Subsequent post hoc tests (Newman-Keuls) compared the effects of 18-MC to baseline.

The average levels of fluid consumption (ml) during the first two sessions (baseline), as well as consumption during the post-injection session and the recovery session, were compared by two-way ANOVA using treatment and session as main factors; this analysis was followed by one-way ANOVAs for each treatment group and post-hoc tests when appropriate.

For the weight gain experiment, the data for all four treatment groups from days 1-21 were analyzed using two-way ANOVA, with treatment and time as main factors. Furthermore, the data for the first two weeks and the last week for water-vehicle, water-18-MC and sucrose 18-MC were analyzed separately using two-ANOVA, with treatment and time as main factors. Post-hoc comparison tests (Fisher LSD tests) were conducted when appropriate.

Example 8

18-MC Reduces Operant Sucrose Self-Administration

The analysis of the operant self-administration data revealed a significant reward×18-MC interaction ($F_{3,20}$=4.30, P<0.02). Post hoc tests showed that only one effect was significant: a dose of 40 mg/kg of 18-MC reduced operant responding for sucrose (p<0.005). See FIG. 1.

Example 9

18-MC Reduces Sucrose Consumption

Figure 2A:
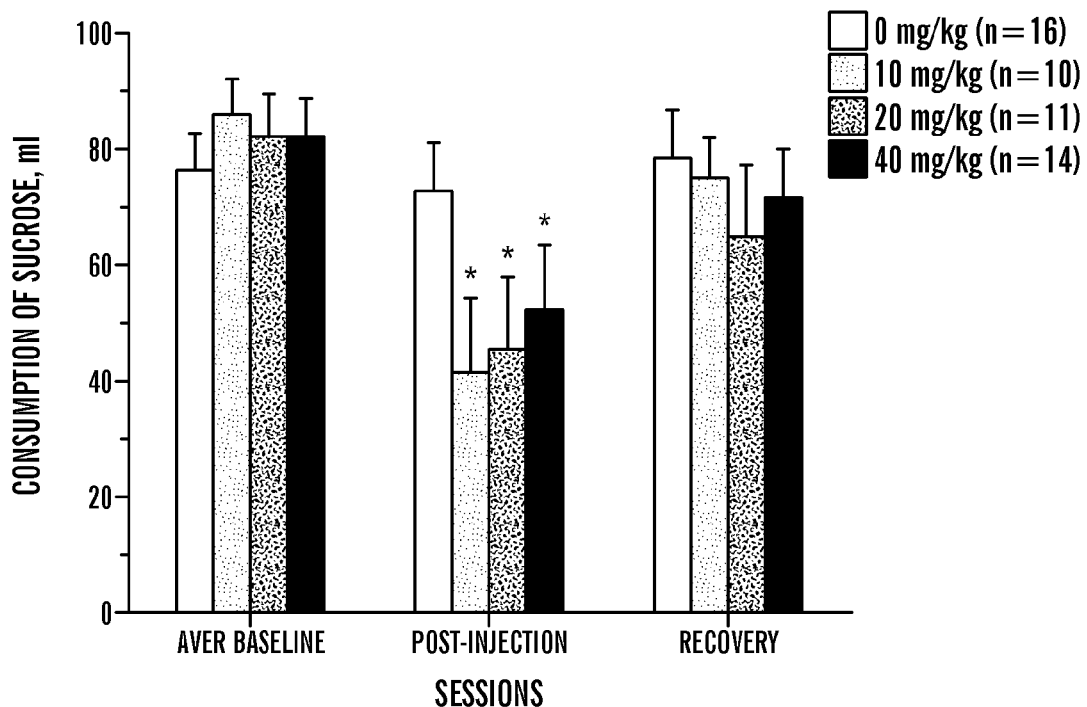
FIGS. 2A-C show bar graphs comparing the average baseline, post-injection, and recovery consumption of sucrose (FIG. 2A), water (FIG. 2B), and total consumption (FIG. 2C) for different mg/kg doses of 18-MC in a two bottle sucrose/water experiment. *, p<0.05, vs baseline, LSD tests.
Figure 2B:
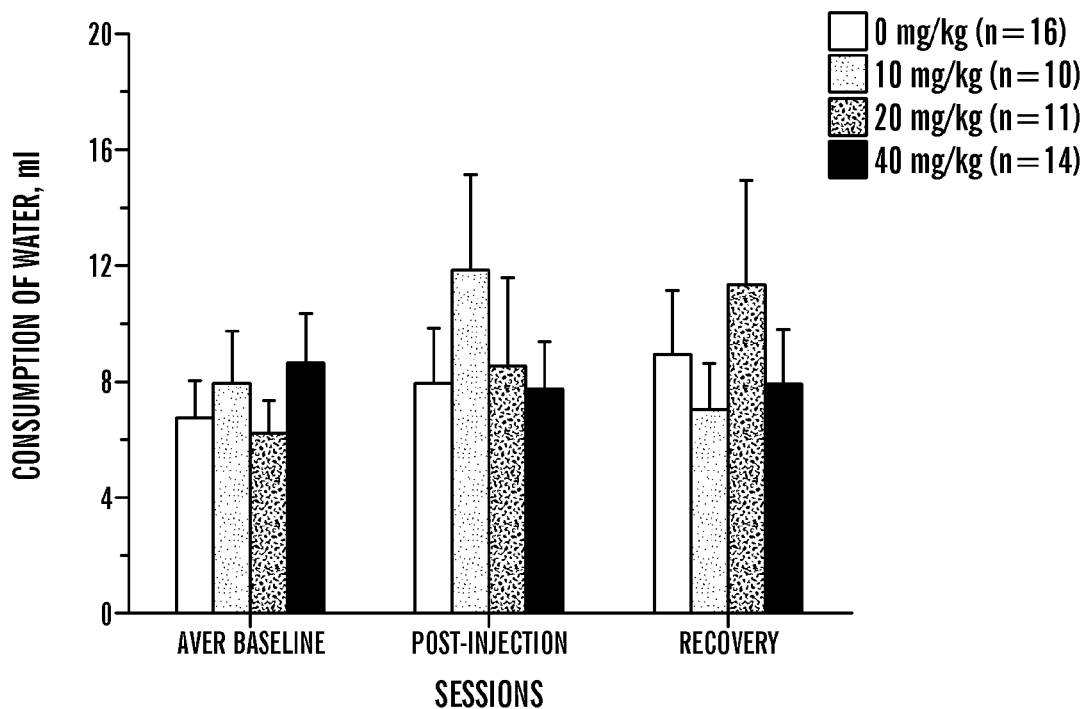

The average basal levels of 5% sucrose solution consumption (ml) in the vehicle- and 18-MC-treated (10, 20 and 40 mg/kg) groups were as follows, respectively: 76.4±6.2; 85.9±6.2; 82.3±7.3; 82.4±6.5 (see FIG. 2A). The average basal levels of water consumption (ml) in the same groups were as follows, respectively: 6.7±1.3; 7.9±1.8; 6.2±1.1; 8.6±1.7 (see FIG. 2B). There were no significant differences in average basal levels of intake of sucrose or water among the four treatment groups (for sucrose: $F_{3,47}$=0.38, P>0.77; for water: $F_{3,47}$=0.52, P>0.67). See FIGS. 2A-C.

The overall ANOVA of sucrose consumption revealed a significant main effect of session (Session effect: $F_{2,94}$=18.35, P<0.00001). Further analysis of sucrose intake for each treatment group suggested that consumption of sucrose remained constant across sessions in the vehicle-injected group, but was significantly reduced in all 18-MC-treated groups (for vehicle: $F_{2,30}$=0.23, P>0.79; for 10 mg/kg: $F_{2,18}$=8.60, P<0.002; for 20 mg/kg: $F_{2,20}$=4.66, P<0.02; for 40 mg/kg: $F_{2,26}$=7.91, P<0.002). As shown in FIG. 2A, all 18-MC-injected animals decreased their sucrose intake levels during the 19-h session immediately following the treatment as compared to their baseline levels; sucrose intake returned to baseline during the recovery session (post-hoc tests). See FIG. 2A.

The analysis of water consumption in the same animals indicated that levels of water intake remained stable across sessions in all treated animals (Session effect: $F_{2,94}$=0.82, P>0.44; Treatment×Session interaction: $F_{6,94}$=0.86, P>0.53; see FIG. 2B).

Figure 2C:
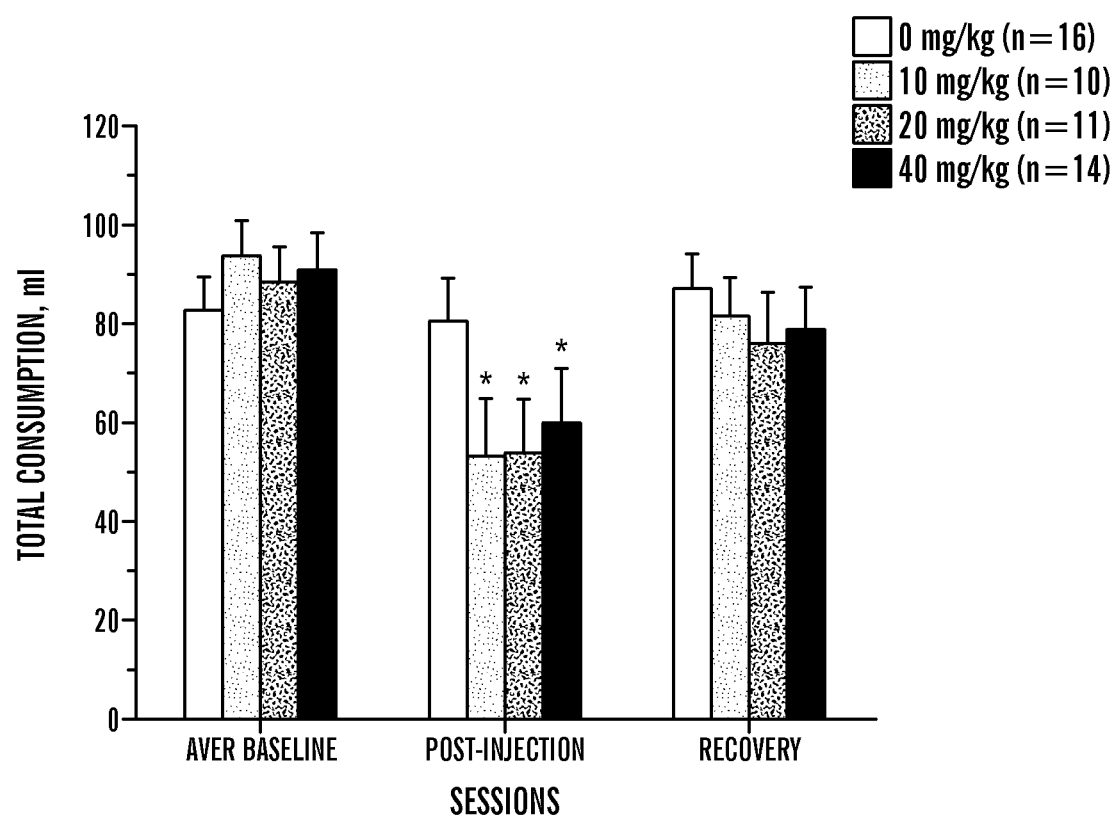

The total fluid consumption data are shown in FIG. 2C. The ANOVA revealed a significant main effect of session and a treatment×session interaction (Session effect: $F_{2,94}$=20.73, P<0.00001; Treatment×Session interaction: $F_{6,94}$=2.25, P<0.05). Subsequent analysis for each treatment group showed that total consumption was reduced during the post-injection session as compared to baseline levels in all groups receiving 18-MC while consumption remained constant in the vehicle-pretreated group (ANOVA for vehicle group: $F_{2,30}$=0.42, P>0.66; for 10 mg/kg: $F_{2,18}$=7.79, P<0.004; for 20 mg/kg: $F_{2,18}$=6.23, P<0.008; for 40 mg/kg: $F_{2,26}$=9.03, P<0.001; post hoc tests). See FIG. 2C.

Example 10

18-MC Reduces Saccharin Consumption

Figure 3A:
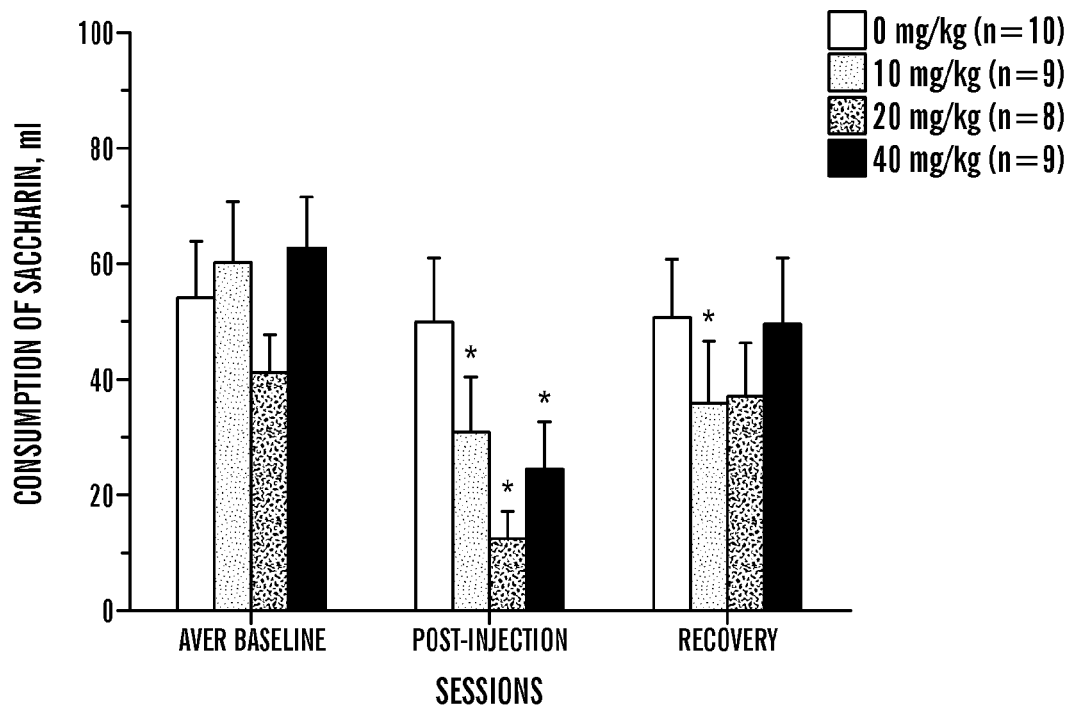
FIGS. 3A-C show bar graphs comparing the average baseline, post-injection, and recovery consumption of saccharin (FIG. 3A), water (FIG. 3B), and total consumption (FIG. 3C) for different mg/kg doses of 18-MC in a two bottle saccharin/water experiment. *, p<0.05, vs. baseline, LSD tests.
Figure 3B:
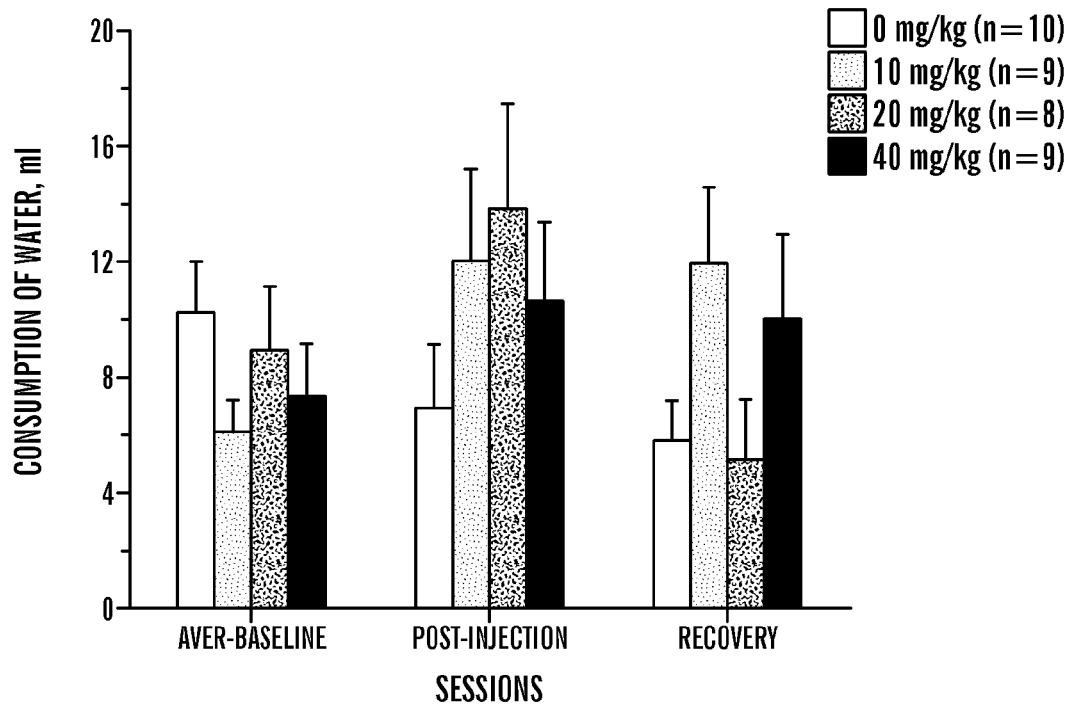

The average basal levels of liquid consumption (ml) in rats treated with vehicle and 18-MC (10, 20, and 40 mg/kg) were as follows for saccharin and water, respectively: 54.2±10.9;

60.3±10.4; 41.1±6.7; 62.6±8.9 and 9.8±2.0; 6.1±1.1; 8.9±2.2; 7.3±1.8 (see FIGS. 3A-B). The levels of saccharin or water were not significantly different among the all treatment groups (for saccharin: $F_{3,32}=1.01$, P>0.40; for water: $F_{3,32}=1.08$, P>0.37). See FIGS. 3A-C.

The analysis of saccharin consumption with ANOVA revealed a significant main effect of session and a significant session×treatment interaction (Session effect: F 2,64=32.61, P<0.00001; Session×Treatment interaction: $F_{6,64}=4.26$, P<0.001). Additional analysis for each treatment group indicated that all dosages of 18-MC resulted in significantly less saccharin intake during the post-injection session as compared to baseline intake (for 10 mg/kg: $F_{2,16}=21.97$, P<0.00003; for 20 mg/kg: $F_{2,14}=7.67$, P<0.006; for 40 mg/kg: $F_{2,16}=15.97$, P<0.0002; post-hoc tests; see FIG. 3A). Interestingly, the group treated with the lowest dose of the drug (i.e., 10 mg/kg) also had reduced intake during the recovery session. The consumption of saccharin in the vehicle-treated group remained unchanged across sessions ($F_{2,18}=0.35$, P<0.71).

Figure 3C:
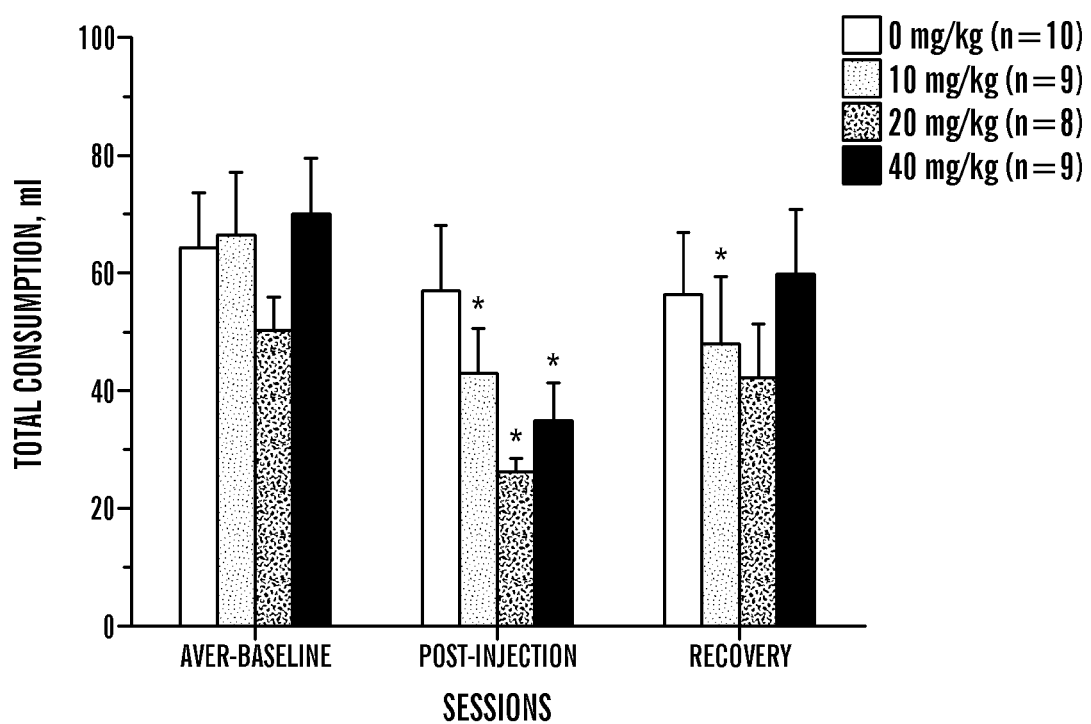

The analysis of water consumption across sessions in the same animals showed that it was not altered by pretreatment with 18-MC (Session effect: $F_{2,64}=2.10$, P>0.13; Treatment×Session interaction: $F_{6,64}=2.20$, P>0.06; see FIG. 3B). The two-way ANOVA of total fluid consumption in this study revealed a significant main effect of session and a significant treatment×session interaction (Session effect: $F_{2,64}=29.89$, P<0.00001; Treatment×Session interaction: $F_{6,64}=2.94$, P<0.01). As shown in FIG. 3C, administration of 18-MC reduced consumption of saccharin during the 19 h after injection in all treatment groups (for 10 mg/kg: $F_{2,16}=9.57$, P<0.002; for 20 mg/kg: $F_{2,14}=7.32$, P<0.007; for 40 mg/kg: $F_{2,16}=14.44$, P<0.0002; post-hoc tests). Furthermore, the effect of the lowest dose of 18-MC (i.e., 10 mg/kg) remained significant during the recovery session. The total fluid consumption in the vehicle-pretreated group remained constant across sessions ($F_{2,18}=1.89$, P>0.20).

Example 11

18-MC Reduces Saline Consumption

Figure 4A:
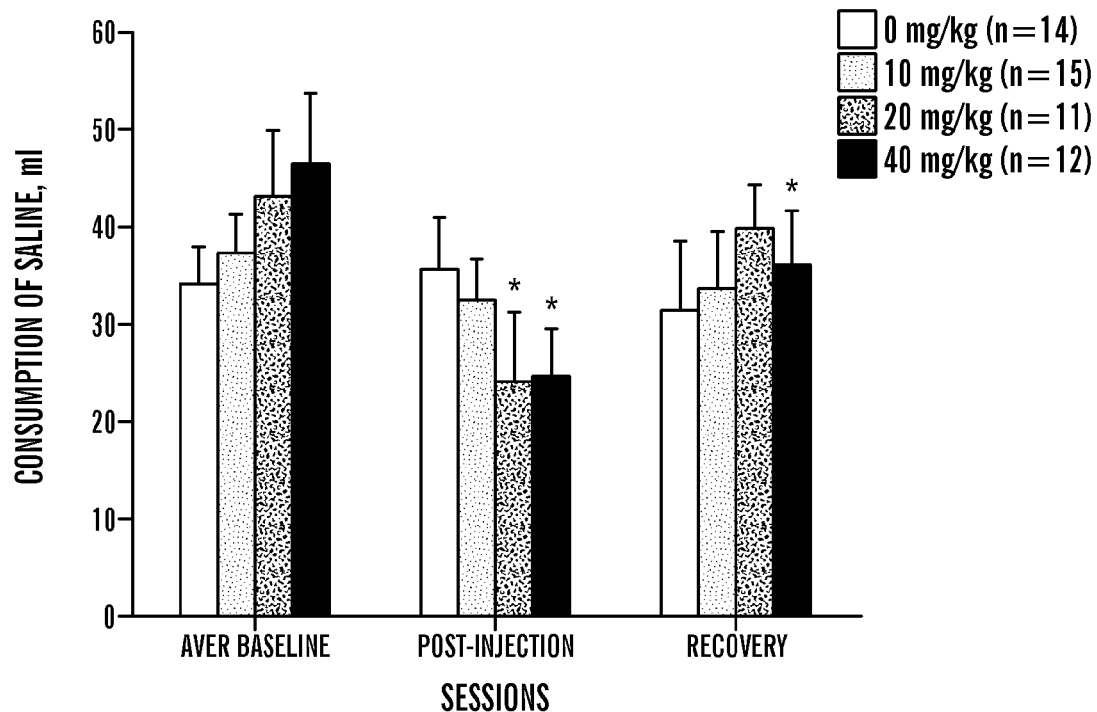
FIGS. 4A-C show bar graphs comparing the average baseline, post-injection, and recovery consumption of saline (FIG. 4A), water (FIG. 4B), and total consumption (FIG. 4C) for different mg/kg doses of 18-MC in a two bottle saline/water experiment. *, p<0.05, vs. baseline, LSD tests.
Figure 4B:
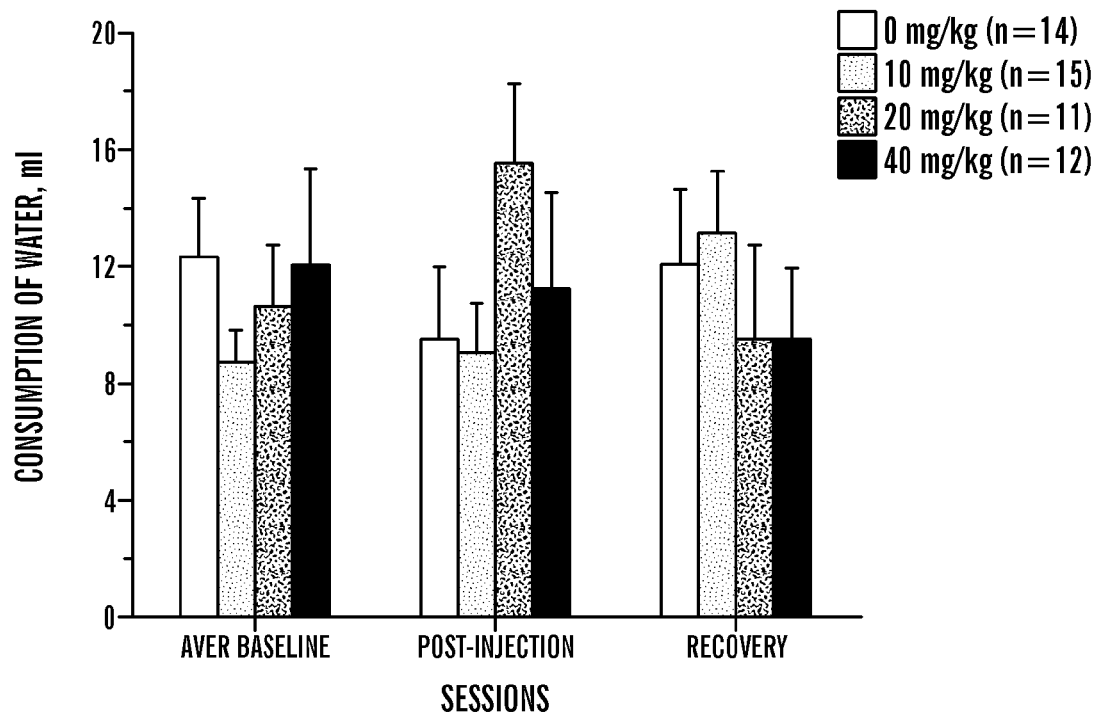
Figure 4C:
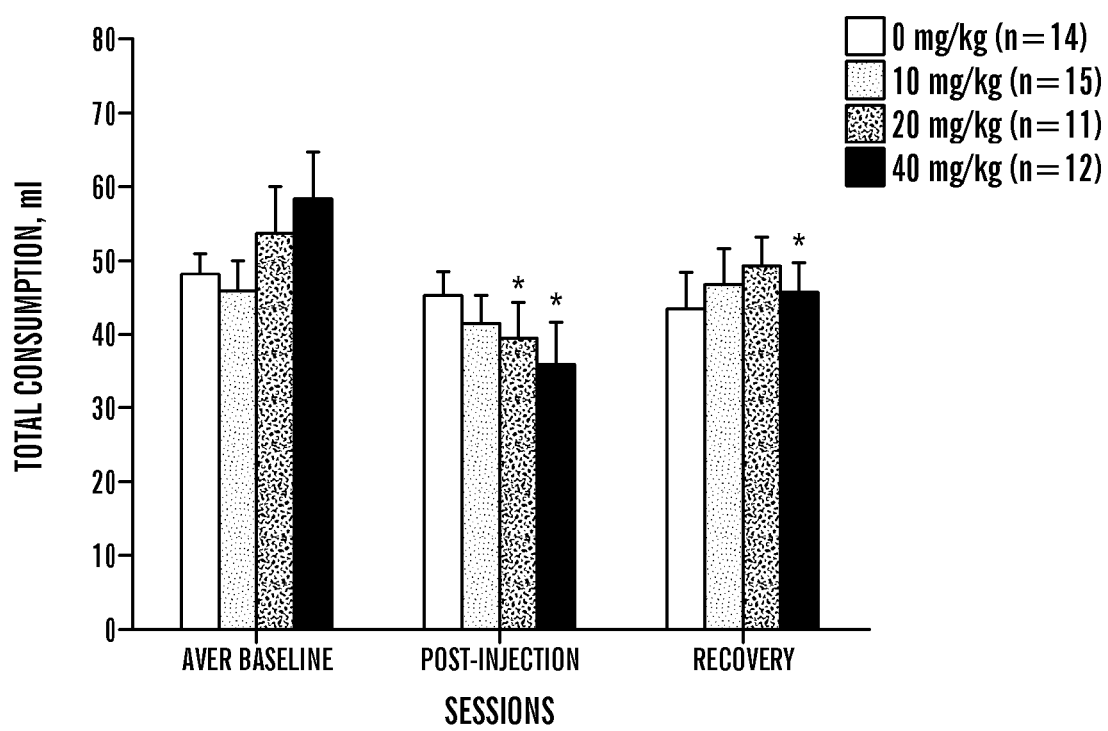

The average basal levels of liquid consumption (ml) in rats treated with vehicle and 18-MC (10, 20 and 40 mg/kg) were as follows for saline and water, respectively: 34.1±3.8; 37.2±4.0; 43.0±6.8; 46.3±7.3 and 12.3±2.0; 8.7±1.1; 10.6±2.1; 12.0±3.3 (see FIGS. 4A-B). The levels of saline or water intake were not significantly different among the all treatment groups (for saline: $F_{3,48}=1.02$, P>0.39; for water: $F_{3,48}=0.63$, P>0.60). See FIGS. 4A-C.

The analysis of saline consumption with ANOVA revealed a significant main effect of session and a significant session×treatment interaction (Session effect: $F_{2,96}=9.41$, P<0.0002; Treatment×Session interaction: $F_{6,96}=2.90$, P<0.01). The analysis of the effect of session for each treatment group showed that consumption of saline was reduced (as compared to the baseline) in the groups pretreated with 20 and 40 mg/kg of 18-MC but remained unchanged in the groups pretreated with 10 mg/kg of 18-MC and vehicle (for 20 mg/kg: $F_{2,20}=8.20$, P<0.003; for 40 mg/kg: $F_{2,22}=9.91$, P<0.001; for 10 mg/kg: $F_{2,28}=0.92$, P>0.41; for vehicle: $F_{2,26}=0.24$, P>0.79). As shown in FIG. 4A, the effects of 20 and 40 mg/kg of 18-MC were significant during the 19 h immediately following injection; an effect of the highest dose of 18-MC was also significant during the recovery session (post hoc tests).

The consumption of water in the same rats was not different across sessions in all treatment groups (Session effect: $F_{2,96}=0.04$, P>0.96; Treatment×Session interaction: $F_{6,96}=1.57$, P>0.16).

The analysis of overall fluid consumption in this study revealed a significant main effect of session and a significant session×treatment interaction (Session effect: $F_{2,96}=20.63$, P<0.0001; Treatment×Session interaction: $F_{6,96}=4.16$, P<0.001). Further one-way ANOVAs for each treatment group showed that total fluid consumption was significantly reduced in the groups pre-treated with 20 and 40 mg/kg of 18-MC, while it remained unchanged in the groups receiving injections of 10 mg/kg of 18-MC and vehicle (for 20 mg/kg: $F_{2,20}=10.63$, P<0.001; for 40 mg/kg: $F_{2,22}=20.50$, P<0.0001; for 10 mg/kg: $F_{2,28}=2.15$, P>0.13; for vehicle: $F_{2,26}=0.71$, P>0.50). As evident from FIG. 4C, the effect of 20 mg/kg 18-MC was significant only during the post-injection session, while the effect of the highest dose of 18-MC was also significant during the recovery session (post-hoc tests).

Example 12

18-MC (40 mg/kg i.p.) Reduces Intake of Water

Figure 5:
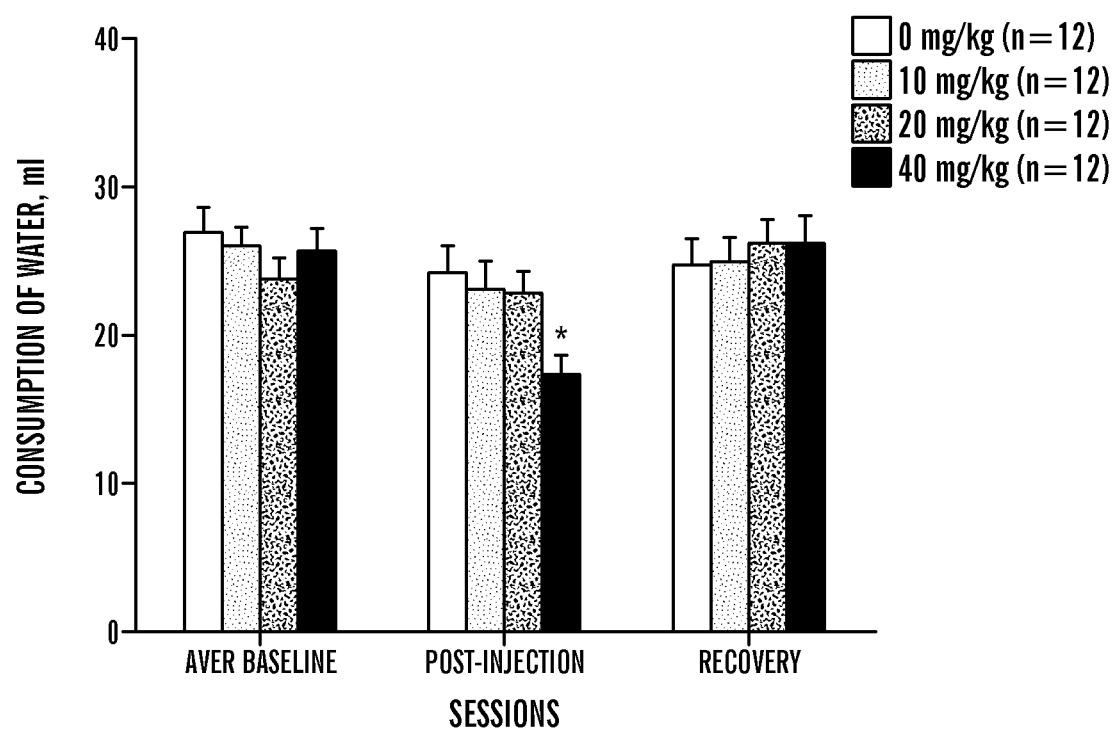
FIG. 5 shows a bar graph comparing the average baseline, post-injection, and recovery consumption of water for different mg/kg doses of 18-MC in a two bottle water/water control. *, p<0.05, vs. baseline, LSD tests.

The average basal levels of water consumption (ml) in rats treated with vehicle and 18-MC (10, 20 and 40 mg/kg) were as follows, respectively: 26.9±1.7; 26.0±1.2; 23.8±1.4; 25.6±1.6 (see FIG. 5). The levels of water intake were not significantly different among the all treatment groups ($F_{3,44}=0.78$, P>0.51). See FIG. 5.

The analysis of water consumption in this study revealed a significant session×treatment interaction (Treatment×Session interaction: $F_{6,88}=3.21$, P<0.007). Further one-way ANOVAs for each treatment group showed that water consumption was significantly reduced in the group treated with 40 mg/kg of 18-MC, while it remained unchanged in all other treatment groups (for 40 mg/kg: $F_{2,22}=15.57$, P<0.00006; for vehicle: $F_{2,22}=2.46$, P>0.11; for 10 mg/kg: $F_{2,22}=1.14$, P>0.34; for 20 mg/kg: $F_{2,22}=2.34$, P>0.12, FIG. 5).

Example 13

18-MC Reduces Sucrose-Induced Body Weight Gain

Figure 6:
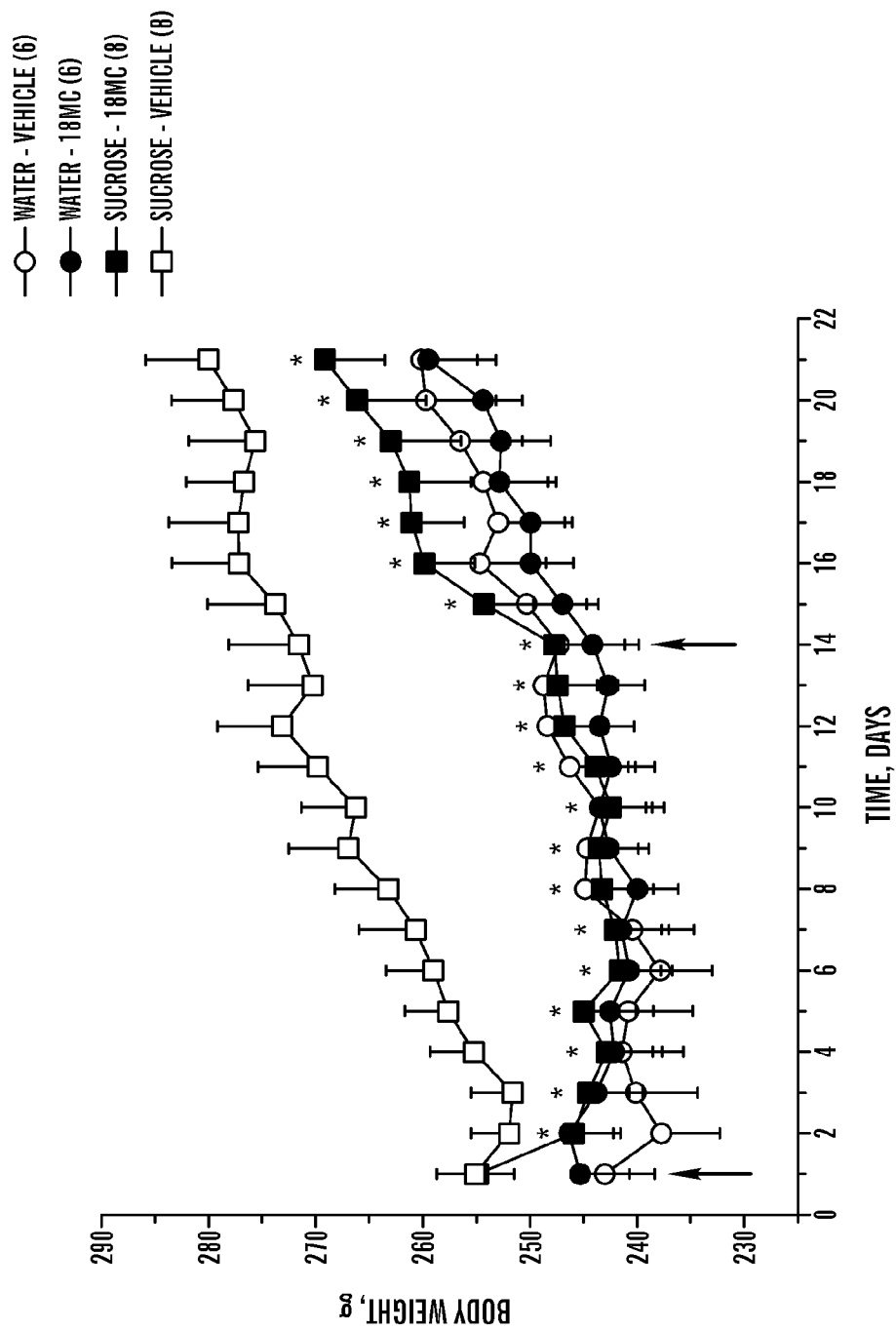
FIG. 6 shows a graph of average weights of rats over 22 days of treatment in water-vehicle, water-18-MC, sucrose-vehicle, and sucrose-18-MC groups. *, p<0.05, sucrose-vehicle vs. sucrose-18-MC; LSD tests.

The average weights of rats before the initiation of treatment (day 1) in water-vehicle, water-18-MC, sucrose-vehicle and sucrose-18-MC groups were as follows, respectively (g SEM): 243.0±4.6; 245.3±4.6; 255.1±3.6; 254.9±3.4. The average weights on day 1 were not significantly different among the treatment groups ($F_{3,24}=2.49$, P>0.09). See FIG. 6. Analysis of data for all treatment groups for the entire three-week period of observation revealed a significant main effect of treatment and a significant treatment×time interaction (Treatment effect: $F_{3,24}=4.47$, P<0.01; Treatment×Time interaction: $F_{60,480}=3.85$, P<0.00001). Further analysis revealed that sucrose-drinking animals pretreated with 18-MC (40 mg/kg i.p.) had significantly lower body weights as compared to the vehicle-treated animals at all time points of observation except for the first one (Treatment effect: $F_{1,14}=6.33$, P<0.025; Treatment×Time interaction: $F_{20,280}=5.60$, P<0.00001; post-hoc tests). Furthermore, during the two weeks of treatment the average weights of rats in the former group were not significantly different from those in either vehicle-treated or 18-MC-treated groups maintained on water (Treatment effect: $F_{2,17}=0.08$, P>0.92). These results indicate that 18-MC reduces body weights of animals consuming a highly caloric sucrose solution, while it has no effect in animals maintained on a normal diet (Treatment effect: $F_{1,10}$=0.001, P>0.97). After cessation of treatment, the weights in the 18-MC-treated sucrose-drinking group were not significantly different from than those in either vehicle-treated group or 18-MC-treated group maintained on water, indicating that recovery of the weight gain in the 18-MC-treated sucrose-drinking group did not occur for another week (Treatment effect: $F_{2,17}$=0.93, P>0.41; Treatment× Time interaction: $F_{12,102}$=0.56, P>0.87).

The present invention disclose the effects of treatment with 18-MC (18-methoxycoronaridine), a selective antagonist at α3β4 nicotinic receptors, on operant self-administration of sucrose, consumption of palatable fluids and sucrose-induce body weight gain. The solutions tested in the two-bottle consumption studies were 5% sucrose, which is palatable and nutritive as well as 0.1% saccharine and 0.6% saline, which are also tasteful for rats but are not nutritive. See Fregly, M. J., et al., *Physiol Behav.*, 51: 915-918 (1992); Hausmann, M., "The Behavior of Albino Rats in Choosing Foods: II. Differentiation Between Sugar and Saccharin" pp. 419-428 (1933); Stefurak, T. L., et al., *Behav. Neurosci.*, 106: 125-139 (1992); and Warwick, Z. S. et al., *Physiol Behav.*, 60: 711-715 (1996), which are hereby incorporated by reference in their entirety.

Consistent with previous reports (see Fregly, M. J., et al., *Physiol Behav.*, 51: 915-918 (1992); Hausmann, M., "The Behavior of Albino Rats in Choosing Foods: II. Differentiation Between Sugar and Saccharin" pp. 419-428 (1933); Hayward, M. D., et al., *Pharmacol. Biochem. Behav.*, 85: 601-611 (2006); and Stewart, R. B. et al., *Alcohol Clin. Exp. Res.*, 18: 375-381 (1994), which are hereby incorporated by reference in their entirety), under basal conditions, all three palatable fluids were preferred to water; however, sucrose was consumed more avidly than the two other solutions. Overall, the two highest dosages of 18-MC (i.e., 20 and 40 mg/kg i.p.) significantly reduced the consumption of all three palatable liquids without affecting water consumption in the same animals. The lowest dose of the drug was effective in reducing the consumption of the two sweet liquids (i.e., sucrose and saccharin) and had no effect on consumption of water in the same groups of rats. Despite there being no changes in water consumption in the above groups, total consumption of fluids was reduced. The lack of compensation with water could be due to the fact that animal's intake of fluids greatly exceeded physiological requirements while drinking sucrose, saccharin, or saline. Consistent with this explanation, in a control experiment (see FIG. 5), animals consumed no more than 25 ml of water over the same 19 h period; this was much less than their consumption of sucrose, saccharin or saline solutions under the same conditions (see FIGS. 2-4). Taken collectively, these findings suggest that 18-MC reduces consumption of palatable fluids regardless of their caloric value.

There was no apparent dose-response effect of 18-MC on consumption of sucrose and saccharin over the range of doses studied, suggesting a ceiling effect at 10 mg/kg. For saline consumption, the ceiling appeared at 20 mg/kg. The apparent long-lasting effects of two treatments (see FIGS. 3A-4A) during the recovery session could possibly be due to an effect of 18-hydroxycoronaridine, an active metabolite present in plasma in low concentrations. See Glick, S. D., et al., *CNS Drug Rev.*, 5: 27-42 (1999) and Zhang, W., et al., *Drug Metab Dispos.*, 30: 663-669 (2002), which are hereby incorporated by reference in their entirety.

As previously mentioned, the effect of 18-MC on water consumption alone was assessed in an identical experimental paradigm. The highest dose of 18-MC reduced consumption of water, while the two other dosages had no significant effect (see FIG. 5). Such effect of 18-MC on water consumption was not present when a choice of another palatable fluid was present (see FIGS. 2-4). This discrepancy could be explained by the fact that basal levels of water consumption were already very low in the latter groups. Nevertheless, the control experiment showed that there was at least four-fold selectivity of 18-MC for reducing consumption of sucrose and saccharin relative to water. Importantly, 18-MC had no effect on water consumption in an operant self-administration paradigm (see FIG. 1), consistent with previous reports from our laboratory. See Glick, S. D., et al., *Brain Res.*, 719: 29-35 (1996) and Glick, S. D., et al., *Psychopharm.*, 139: 274-280 (1998), which are hereby incorporated by reference in their entirety.

The mechanism of 18-MC's effects on consumption of palatable fluids may involve an alteration in taste perception, or changes in central neurotransmission mediating reward. For example, 18-MC could enhance the expression of gustducin-IR cells on the taste buds (see Wong, G. T. et al., *Nature*, 381: 796-800 (1996), which is hereby incorporated by reference in its entirety), and thus increase sensitivity of the tongue to the sweet stimuli reducing sucrose and saccharine intake. Exposure to nicotine was previously shown to affect the same cells and increase appetite to salty and sweet substances in animals and humans. See Jias, L. M., et al., *Pharmacol. Biochem. Behav.*, 35: 489-491 (1990); Sato, K., et al., "Sensitivity of Three Loci on the Tongue and Soft Palate to Four Basic Tastes in Smokers and Non-Smokers" pp. 74-82 (2002); and Tomassini, S. et al., *Neuroscience*, 147: 803-810 (2007), which are hereby incorporated by reference in their entirety. Alternatively, 18-MC could block nicotinic receptors located in the nucleus of the solitary tract, a brain stem structure responsible for recognition of basic taste qualities in rats. See Dhar, S., et al., *Am. J. Physiol Regul. Integr. Comp Physiol*, 279: R132-R140 (2000) and Roussin, A. T., et al., *J. Neurophysiol.* (2007), which are hereby incorporated by reference in their entirety. This effect could increase sensitivity to sweet or salty taste and reduce consumption of the palatable fluids. 18-MC could also indirectly attenuate sucrose-induced dopamine release in the nucleus accumbens (see Di Chiara, G., *Eur. J. Pharmacol.*, 375: 13-30 (1999), which is hereby incorporated by reference in its entirety) and attenuate sucrose reward, thus preventing excessive intake of the tested substances. 18-MC's effect on operant self-administration of sucrose in the present study (see FIG. 1) is consistent with this premise. Such effect could be achieved via the antagonism of α3β4 nicotinic receptors located in the nuclei of the habenulo-interpeduncular pathway, known to mediate 18-MC's effects on self-administration of morphine and morphine-induced sensitization of the mesolimbic pathway. See Glick, S. D., et al., *Psychopharmacology* (Berl), 139: 274-280 (1998); Quick, M. W., et al., *Neuropharmacology*, 38: 769-783 (1999), which are hereby incorporated by reference in their entirety. 18-Methoxycoronaridine acts in the medial habenula to attenuate opioid reward and mesolimbic dopamine sensitization to morphine. See Glick, S. D., et al., *Europ. J. Pharmacol.*, 537:94-98 (2006) and Taraschenko, O. D., et al., *Synapse*, 61: 547-560 (2007), which are hereby incorporated by reference in their entirety.

Previous studies with intermittent access to sucrose showed that rats maintained on normal chow tend to decrease their chow intake in order to compensate for excess caloric intake from sucrose solution; this adjustment may result in unchanged body weights throughout an experiment See Avena, N. M., et al., *Neuroscience*, 122: 17-20 (2003) and Colantuoni, C., et al., *Obes. Res.*, 10: 478-488 (2002), which are hereby incorporated by reference in their entirety. Thus, in order to better characterize the effects of 18-MC on weight gain, a highly concentrated sucrose solution was made available continuously throughout the three weeks of experiment. Daily injection of 18-MC (20 mg/kg i.p. for two weeks) attenuated sucrose-induced weight gain in rats on normal chow, while it had no effect on the body weight of rats maintained on water and chow. Neither food nor sucrose intake was assessed in this experiment; however, since food intake is a major determinant of body weight, it is conceivable that 18-MC decreased consumption of chow along with an attenuation of sucrose intake. The mechanism of this effect remains to be determined and may involve nicotinic-receptor mediated alteration of complex homeostatic systems of energy expenditure in the brain and in the periphery. See Jo, Y. H., et al., *J. Neurobiol.*, 53: 618-632 (2002), which is hereby incorporated by reference in its entirety. For example, downstream effects of 18-MC's antagonism at U304 nicotinic receptors could mimic those of prolonged exposure to nicotine and nicotine-induced desensitization of the same receptors. See Alkondon, M., et al., *J. Pharmacol. Exp. Ther.*, 313: 740-750 (2005) and Giniatullin, R., et al., *Trends Neurosci.*, 28: 371-378 (2005), which are hereby incorporated by reference in their entirety. Given the fact that nicotine-induced anorexia is linked to low body weight in smokers and nicotine-exposed animals, 18-MC could reduce body weight by similar a mechanism. See Blaha, V., et al., *Acta Medica*. (Hradec, Kralove), 41: 167-173 (1998) and Bray, G. A., *Int. J. Obes. Relat-Metab Disord.*, 24 Suppl 2: S8-17 (2000), which are hereby incorporated by reference in their entirety. Possible sites for 18-MC's action may include the nucleus of the solitary tract, the area postrema, and parasympathetic ganglia of the gastrointestinal tract. These areas express high levels of $\alpha3\beta4$ nicotinic receptors and are known to be involved in feeding behavior. See Berthoud, H. R., *Neurosci. Biobehav. Rev.*, 26: 393-428 (2002); Di Angelantonio, S., et al., *Eur. J. Neurosci.*, 17: 2313-2322 (2003); Jo, Y. H., et al., *J. Neurobiol.*, 53: 618-632 (2002); and Nguyen, H. N., et al., *J. Pharmacol. Exp. Ther.*, 307: 1090-1097 (2003), which are hereby incorporated by reference in their entirety.

In conclusion, acute systemic administration of 18-MC reduces operant self-administration of sucrose and reduces ad libitu intake of sucrose, saccharin, and saline. Furthermore, repeated administration of 18-MC reduces sucrose-induced weight gain in rats. Although the precise mechanisms of these effects are not clear at this time, 18-MC deserves further attention as a potential treatment for obesity.

Example 14

18-MC Inhibits Operant Responding for Sucrose

Figure 7:
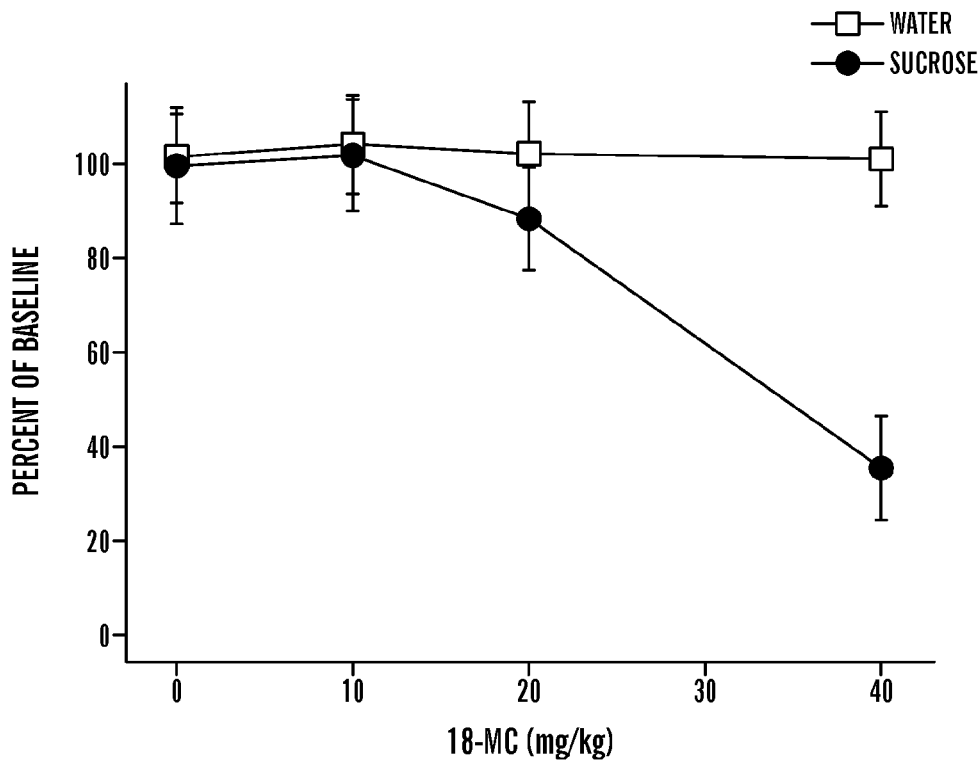
FIG. 7 shows a graph of dose dependant suppression of response for sucrose compared to water. Rats weighing approximately 250 g were trained to self-administer 15% sucrose (0.01 ml/barpress) or water (0.01 ml/barpress) during daily one hour test sessions. 18-MC (40 mg/kg, i.p.), administered 15 minutes prior to the session, significantly (p<0.02) decreased responding for sucrose while having no effect on responding for water. N=6/group.

Based on animal studies, using well established models, 18-MC has been shown to have the potential to successfully treat multiple forms of drug addiction (e.g., cocaine, heroin, alcohol, and smoking). 18-MC dose-dependently decreases morphine self-administration in rats. These effects are selective in that the same doses of 18-MC do not affect responding for water, a non-drug reinforcer. Other studies demonstrated that 18-MC also decreases cocaine, methamphetamine and nicotine self-administration in rats. Other work has extended the "anti-addictive" effect of 18-MC to oral intake of ethanol. In all cases, these effects last for at least 24 hours. It is important to note that 18-MC has no motor effects at any of these times. Unlike 18-MC, ibogaine and many other iboga alkaloid congeners (approximately 30 tested) decrease responding for water as well as for drugs. And it was precisely this unique specificity that led to development and study of 18-MC. Thus, substantial data supported the use of water-reinforced responding as a control for nonspecific treatment effects (in fact, several agents were more effective in suppressing responding for water than for drugs). Nevertheless, it was eventually decided to adopt a new control using satiated rats responding for a sweet solution containing either saccharin (0.15-1.2% w/v) or sucrose (10-20% w/v); baseline rates from one day to the next proved to be much more variable with saccharin than with sucrose and sucrose was chosen. Rates of responding for 10, 15, and 20% sucrose encompassed the range of most drug self-administration rates, and at a dose (20 mg/kg, i.p.) that significantly decreases drug self-administration by 40-80% (depending on the drug), 18-MC had no significant effect (10-20% decreases) on sucrose responding. However, subsequent studies conducted more recently showed that, at a higher dose (40 mg/kg, i.p.), 18-MC did indeed decrease responding for sucrose (see FIG. 7).

Example 15

Figure 8:
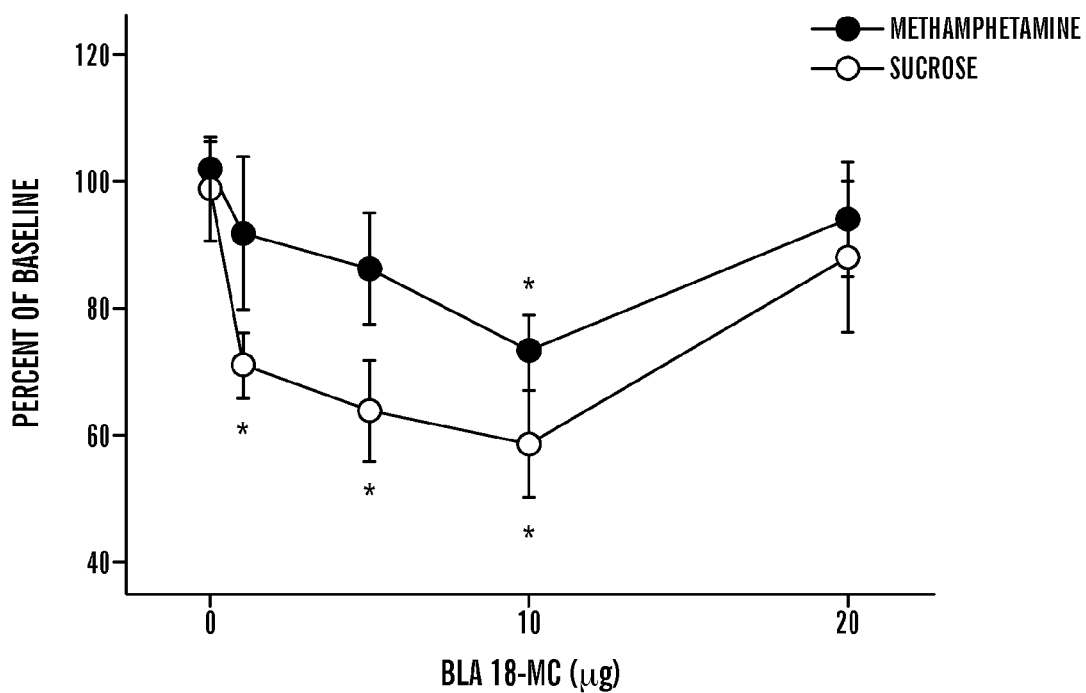
FIG. 8 is a graph showing effects of local infusion of 18-MC into the basolateral amygdala on methamphetamine self-administration and responding for sucrose. Baseline methamphetamine infusions averaged (S.E.M.) 20.2±0.9 while baseline responding for sucrose averaged (S.E.M.) 27.1±2.1. Each data point represents the mean (S.E.M.) percent of baseline of 6-9 rats. (*=p<0.05-0.01).

Local Administration of 18-MC into the Dorsolateral Tegmentum or Basolateral Amygdala Decreases Operant Responding for Sucrose Although the medial habenula and the interpeduncular nucleus are the brain regions having the highest concentrations of $\alpha3\beta4$ nicotinic receptors, moderate densities of these receptors are localized in the ventral tegmental area, in the basolateral amygdala, and in the dorsolateral tegmentum (caudal pedunculopontine and laterodorsal tegmental nuclei). The dorsolateral tegmentum contains the cell bodies of cholinergic neurons projecting to the ventral tegmental area and has already been shown to be involved in drug self-administration. The basolateral amygdala has also been very much implicated in reward-related phenomena, and associated with both stimulants and sucrose. Accordingly, to further investigate brain sites mediating 18-MC's effects on drug self-administration, it was determined if local administration of 18-MC into the dorsolateral tegmentum or basolateral amygdala would alter drug self-administration, the other three sites having already been examined. As done previously, sucrose (15%) was used as a control, non-drug reinforcer. Previously, local administration of 18-MC had no effect on responding for sucrose regardless of whether it was infused into the medial habenula, interpeduncular nucleus, or ventral tegmental area. However, while local administration of 18-MC into the dorsolateral tegmentum had no effect on morphine or methamphetamine self-administration, the same 18-MC treatment decreased responding for sucrose. The neural substrates for 18-MC's effects on morphine and sucrose self-administration clearly appear to be different, although both may involve $\alpha3\beta4$ nicotinic receptors. Interestingly, local administration of 18-MC into the basolateral amygdala decreased both methamphetamine self-administration and responding for sucrose (see FIG. 8), so as noted above, there appears to be some commonality in the neural substrates for stimulant and sucrose reward.

Example 16

Figure 9:
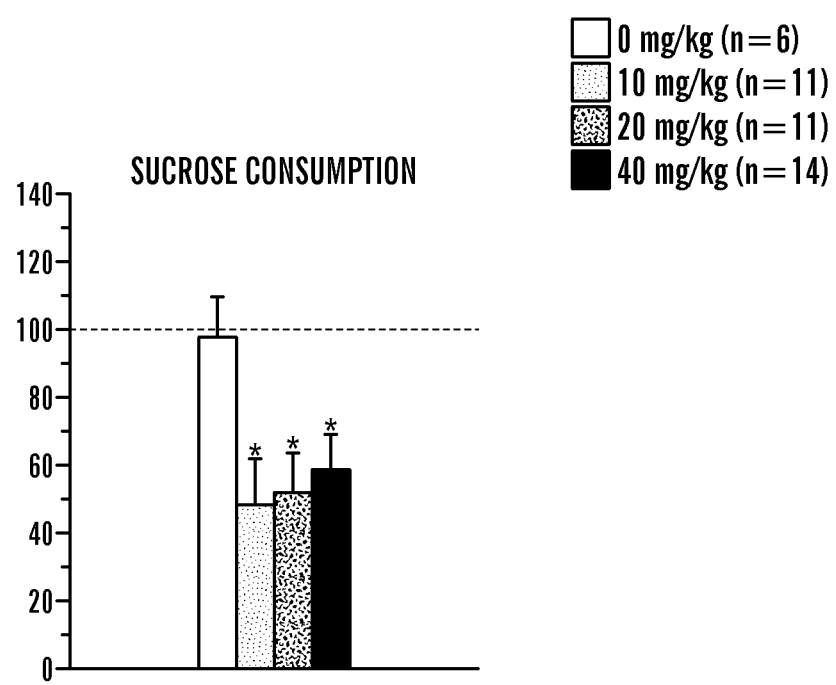
FIG. 9 is a graph showing effects of 18-MC (10, 20, 40 mg/kg i.p.) on consumption of sucrose. Each bar represents mean 24 hour consumption of 5% sucrose solution expressed as percent of baseline (S.E.M.): *=p<0.05.
Figure 10:
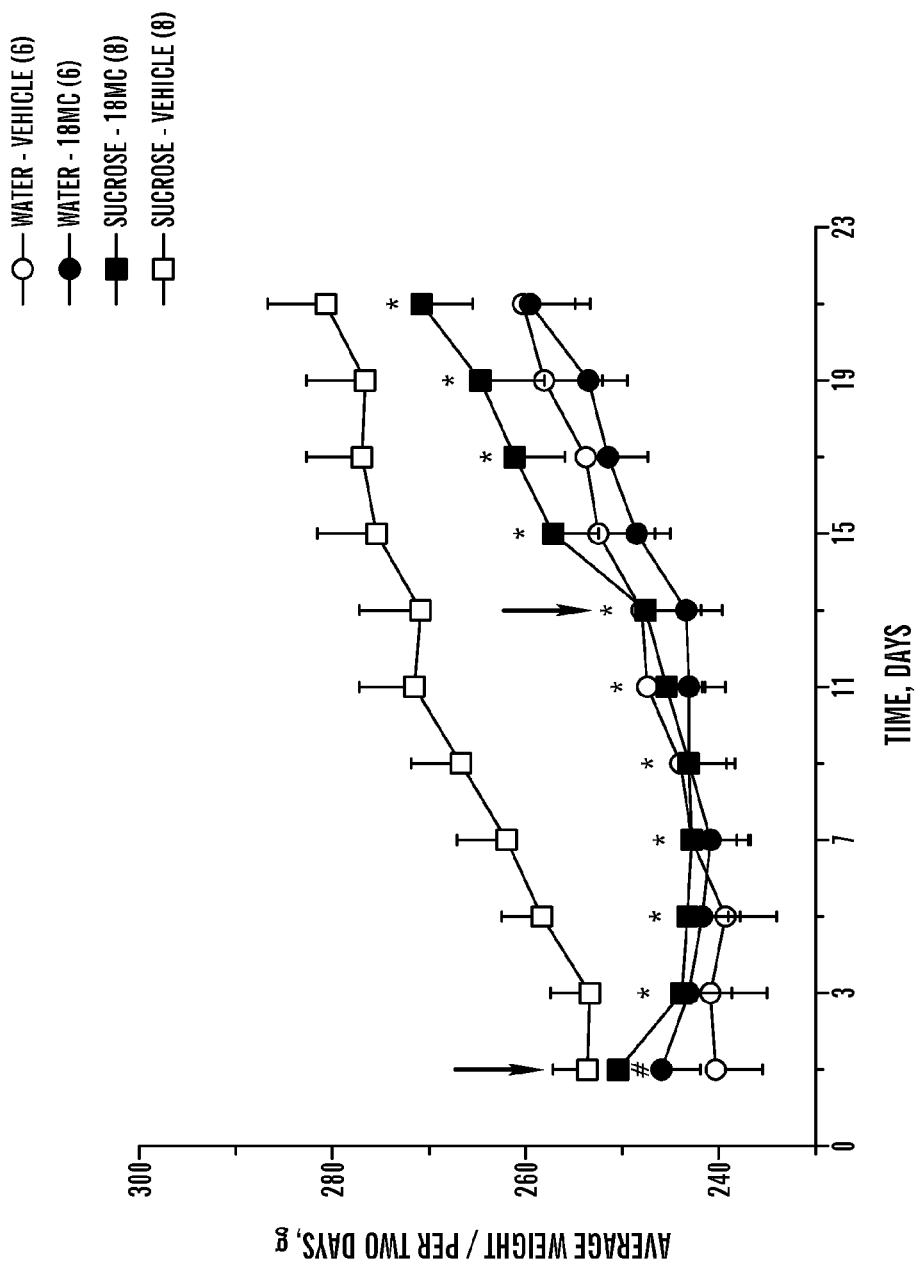
FIG. 10 is a graph showing effects of 18-MC (20 mg/kg i.p.) on weight gain of rats. Arrows indicate the beginning and end of treatment with 18-MC. *=p<0.05, water-vehicle, water-18-MC, sucrose-18-MC vs sucrose-vehicle.
Figure 11:
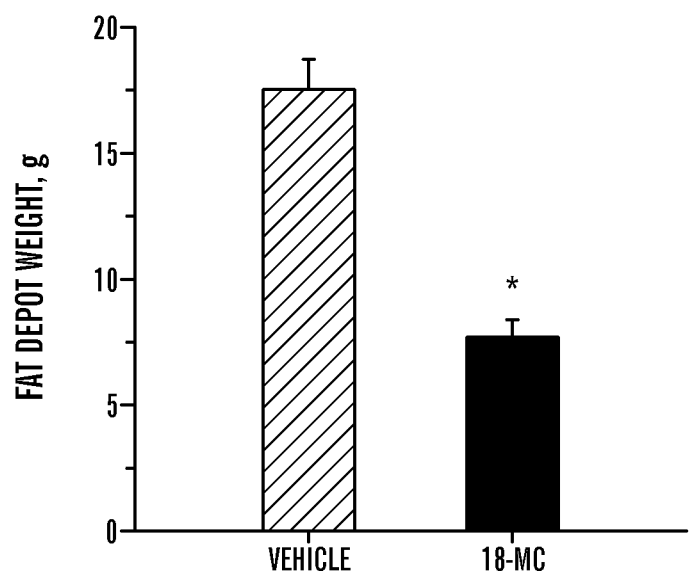
FIG. 11 is a graph showing effects of repeated administration of 18-MC (20 mg/kg i.p. for 14 days) on body fat depots (mean±SEM). *=p<0.05. On the seventh day after the last injection of 18-MC, animals were euthanized in $CO_2$ chambers and decapitated. Necropsies were performed to remove periovarian, perirenal and inguinal fat pads.

18-MC Decreases Oral Intake of Sucrose, Prevents Sucrose-Induced Weight Gain, and Reduces (or Prevents Increases in) Fat Depots As described above, systemic 18-MC can decrease operant responding for sucrose and local administration of 18-MC into the dorsolateral tegmentum can also do so. These findings, which were unanticipated, led to investigation of the possibility that 18-MC might be useful in decreasing intake of sweet substances when available ad libitum along with normal rat chow. Rats offered a choice of drinking sucrose (15%) or water have strong preferences (70-80%) for sucrose. FIG. 9 shows that, over the 24 hours following administration, 18-MC (10-40 mg/kg, i.p.) decreased intake of sucrose; there was no significant effect on water intake. The fact that the effects were similar over the dose range examined suggests that ad libitu sucrose intake is quite sensitive to 18-MC but that there is a ceiling (10 mg/kg) beyond which no further effect occurs (and presumably the effect is dose-related from 0 to 10 mg/kg). Whether 18-MC's effect on sucrose intake has a consequence in terms of body weight regulation was explored in a subsequent study. Rats given unlimited access to sucrose (30%) for two weeks gained excessive weight, consistent with other studies of sucrose-induced obesity. As shown in FIG. 10, daily treatment with 18-MC (20 mg/kg) totally prevented the excessive weight gain attributable to sucrose intake and, as shown in FIG. 11, 18-MC also decreased the weights of rats' fat depots. 18-MC had no effect on the body weight of "normal" rats having only water available. The data suggest that 18-MC might be useful in treating human obesity.

Example 17

18-MC Prevents Excessive Weight Gain Induced by a High Fat Diet

Figure 12:
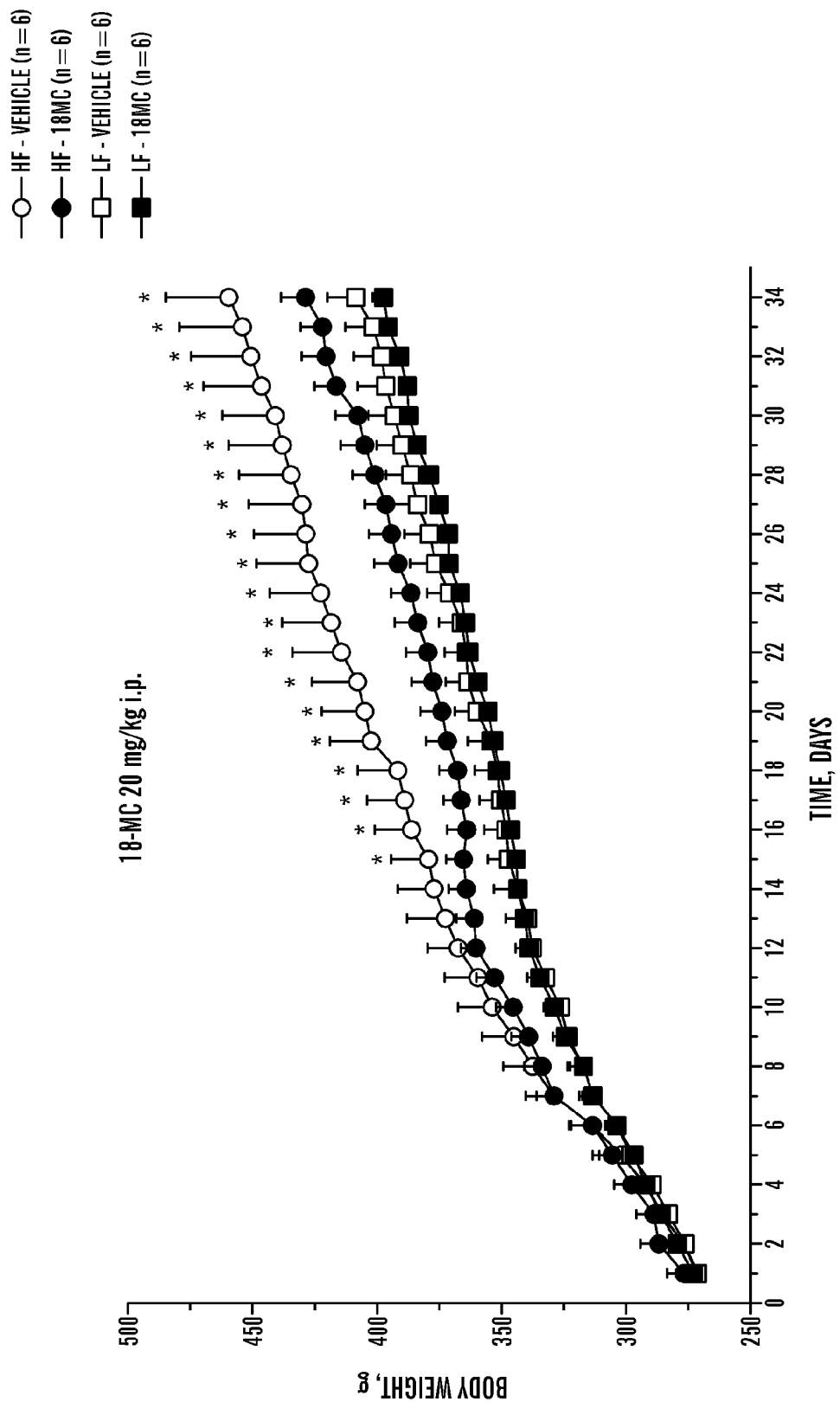
FIG. 12 is a graph showing effects of 18-MC (20 mg/kg i.p.) on weight gain of rats. Each data point represents daily weight (g, ±S.E.M.) of rats having access to high fat (HF) or low fat (LF) diet and water, and treated with 18-MC or vehicle. The black bar indicates the duration of treatment with 18-MC: =<0.05, 18-MC vs vehicle.

The development of obesity in rats maintained on a high fat diet is perhaps the commonly used animal model of diet-induced obesity. Accordingly, the effects of 18-MC (20 mg/kg, i.p. for two weeks) on the weight gain of rats maintained on either high (HF) or low fat (LF) diets ((45 kcal % fat vs. 10 kcal % fat; Research Diets Inc.) was assessed. As shown in FIG. 12, daily treatment with 18-MC (20 mg/kg) totally prevented the excessive weight gain attributable to the high fat diet. 18-MC also significantly decreased, by about 35%, the weights of fat depots in HF rats but not in LF rats.

Previous research has established that 18-MC reduces the reinforcing effects of addictive drugs. These effects appear to be mediated by 18-MC acting as a noncompetitive antagonist at α3β4 receptors in the medial habenula and interpeduncular nucleus. 18-MC also reduces operant responding for sucrose, an effect that appears to be mediated by an action in the dorsolateral tegmentum and basolateral amygdala. Consistent with the operant data, 18-MC reduces oral ad libitu sucrose intake and, when administered daily over two weeks, 18-MC blocks the excessive weight gain attributable to sucrose intake. Similarly, daily administration of 18-MC for two weeks also blocks the excessive weight gain induced by a high fat diet. These and other data suggest that 18-MC may be useful in modulating appetite and treating obesity.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of treating diet-induced obesity in an obese subject, said method comprising:
   selecting an obese subject having diet-induced obesity, and administering to the selected obese subject a compound of the formula:

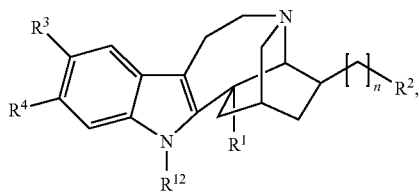

wherein
   n is from 0 to 8;
   $R^1$ is $CH_2OH$, $CH(OH)R^5$, $CH_2OR^5$, $CO_2R^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$;
   $R^2$ is H, unsubstituted or substituted alkyl, YH, $YR^8$, $YR^8R^9$, $YR^8YR^9YR^{10}$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, or $NR^8C(O)R^9$;
   $R^3$ and $R^4$ are the same or different and are selected from the group consisting of H, halogens, unsubstituted or substituted alkyl, OH, $OR^{10}$, $NH_2$, $NHR^{10}$, $NR^{10}R^{11}$, $NHC(O)R^{10}$, or $NR^{10}C(O)R^{11}$;
   $R^5$, $R^6$, $R^7$, $R^8$, $R^9$, $R^{10}$, and $R^{11}$ are the same or different and are selected from the group consisting of H, unsubstituted alkyl, substituted alkyl, unsubstituted aryl and substituted aryl;
   $R^{12}$ is selected from the group consisting of H, unsubstituted alkyl, and substituted alkyl; and
   Y is O or S;
or a pharmaceutically acceptable salt thereof;
under conditions effective to treat diet-induced obesity.

2. The method of claim 1, wherein the subject is a human.
3. The method of claim 1, wherein $R^3$ and $R^4$ are H.
4. The method of claim 1, wherein $R^{12}$ is H.
5. The method of claim 1, wherein $R^1$ is $CO_2R^5$.
6. The method of claim 5, wherein $R^5$ is $CH_3$.
7. The method of claim 1, wherein $R^1$ is $CH_2OH$.
8. The method of claim 1, wherein n is 2 and $R^2$ is $YR^8$.
9. The method of claim 8, wherein Y is O.
10. The method of claim 9, wherein $R^8$ is $CH_3$.
11. The method of claim 9, wherein $R^8$ is $CH_2Ph$.
12. The method of claim 8, wherein $R^8$ is $CH_2OCH_2CH_2OCH_3$.
13. The method of claim 1, wherein n is 2 and $R^2$ is YH.
14. The method of claim 13, wherein Y is O.
15. The method of claim 1, wherein n is 2 and $R^2$ is $YC(O)R^8$.
16. The method of claim 15, wherein Y is O.
17. The method of claim 16, wherein $R^8$ is $(CH_2)_mCH_3$ and wherein m is from 0 to 20.
18. The method of claim 17, wherein m is 10.
19. The method of claim 1, wherein the compound has the formula:

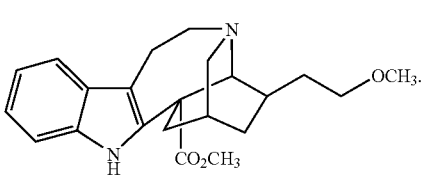 [SMILES: COCCC1CC2CN3CCc4c([nH]c5ccccc45)C(C(=O)OC)(C2)C13]

20. The method of claim 1, wherein the compound has the formula:

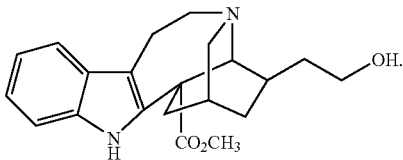 [SMILES: COC(=O)C12CC3CC(CCO)C1N(CCc1c2[nH]c2ccccc12)C3]

21. The method of claim 1, wherein the compound has the formula:

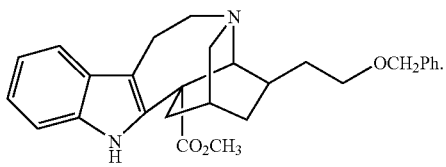

22. The method of claim 1, wherein the compound has the formula:

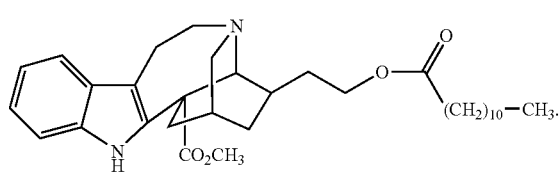

23. The method of claim 1, wherein the compound has the formula:

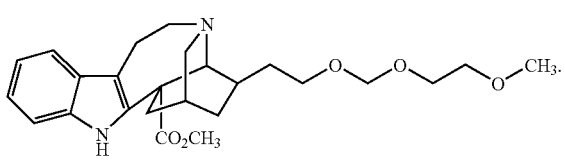 [SMILES: COCCOCOCCC1CC2CN3CCc4c([nH]c5ccccc45)C(C(=O)OC)(C2)C13]

24. The method of claim 1, wherein the compound has the formula:

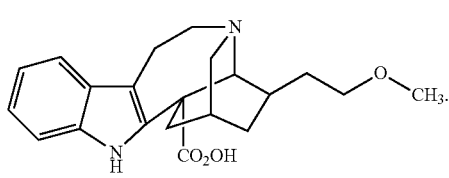

25. The method of claim 1, wherein the administering is selected from the group consisting of orally, topically, parenterally, subcutaneously, intravenously, intramuscularly, intraperitoneally, intranasal instillation, application to mucous membranes, intraventricularly, intracerebrally, rectally, and combinations thereof.

26. The method of claim 1, wherein the compound is administered as a composition comprising a pharmaceutically acceptable carrier.

27. The method of claim 1, wherein said administering comprises administering a dosage comprising 10 to 40 mg/kg of the compound.

28. The method of claim 27, wherein said administering comprises:
administering the dose of the compound once daily.

29. The method of claim 1, wherein the diet is high in fat and contains at least 45 kcal % fat.

30. The method of claim 1, wherein said selected obese subject has a body mass index greater than 25.

31. A method of preventing weight gain in a subject, said method comprising:
selecting a subject susceptible to diet-induced obesity, and administering to the selected subject a compound of the formula:

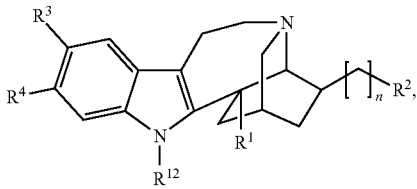

wherein
n is from 0 to 8;
$R^1$ is $CH_2OH$, $CH(OH)R^5$, $CH_2OR^5$, $CO_2R^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$;
$R^2$ is H, unsubstituted or substituted alkyl, YH, $YR^8$, $YR^8R^9$, $YR^8YR^9YR^{10}$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, or $NR^8C(O)R^9$;
$R^3$ and $R^4$ are the same or different and are selected from the group consisting of H, halogens, unsubstituted or substituted alkyl, OH, $OR^{10}R^{11}$, $NHC(O)R^{10}$, or $NR^{10}C(O)R^{11}$;
$R^5$, $R^6$, $R^7$, $R^8$, $R^9$, $R^{10}$, and $R^{11}$ are the same or different and are selected from the group consisting of H, unsubstituted alkyl, substituted alkyl, unsubstituted aryl and substituted aryl;
$R^{12}$ is selected from the group consisting of H, unsubstituted alkyl, and substituted alkyl; and
Y is O or S;
or a pharmaceutically acceptable salt thereof;
under conditions effective to prevent weight gain resulting from diet-induced obesity.

32. The method of claim 1, wherein the diet-induced obesity is sucrose-induced obesity or fat-induced obesity.

33. The method of claim 31, wherein the diet-induced obesity is sucrose-induced obesity or fat-induced obesity.

* * * * *

UNITED STATES PATENT AND TRADEMARK OFFICE
CERTIFICATE OF CORRECTION

PATENT NO. : 8,993,559 B2  Page 1 of 1
APPLICATION NO. : 12/360434
DATED : March 31, 2015
INVENTOR(S) : Glick et al.

It is certified that error appears in the above-identified patent and that said Letters Patent is hereby corrected as shown below:

In the Claims

Column 26, claim 31, lines 43-46, delete:

"$R^3$ and $R^4$ are the same or different and are selected from the group consisting of H, halogens, unsubstituted or substituted alkyl, OH, $OR^{10}$ $R^{11}$, $NHC(O)R^{10}$, or $NR^{10}C(O)R^{11}$."

and insert

-- $R^3$ and $R^4$ are the same or different and are selected from the group consisting of H, halogens, unsubstituted or substituted alkyl, OH, $OR^{10}$, $NH_2$, $NHR^{10}$, $NR^{10}R^{11}$, $NHC(O)R^{10}$, or $NR^{10}C(O)R^{11}$. --

Signed and Sealed this
Fifteenth Day of September, 2015

Michelle K. Lee
*Director of the United States Patent and Trademark Office*